US009130178B2

(12) United States Patent
Yersin et al.

(10) Patent No.: US 9,130,178 B2
(45) Date of Patent: Sep. 8, 2015

(54) OLIGOMERS OF ISONITRILE-METAL COMPLEXES AS TRIPLET EMITTERS FOR OLED APPLICATIONS

(75) Inventors: Hartmut Yersin, Sinzing (DE); Uwe Monkowius, Linz (AT); Tobias Fischer, Rimbach (DE); Walter Finkenzeller, Weihmichl (DE); Rafal Czerwieniec, Regensburg (DE)

(73) Assignee: Merck Patent GmbH (DE)

( * ) Notice: Subject to any disclaimer, the term of this patent is extended or adjusted under 35 U.S.C. 154(b) by 1255 days.

(21) Appl. No.: 12/306,957

(22) PCT Filed: Jul. 3, 2007

(86) PCT No.: PCT/EP2007/005882
§ 371 (c)(1),
(2), (4) Date: Dec. 10, 2009

(87) PCT Pub. No.: WO2008/003464
PCT Pub. Date: Jan. 10, 2008

(65) Prior Publication Data
US 2010/0141120 A1    Jun. 10, 2010

(30) Foreign Application Priority Data
Jul. 4, 2006 (DE) .................. 10 2006 030 860

(51) Int. Cl.
*H01L 51/54* (2006.01)
*C09K 11/06* (2006.01)
*H01L 51/00* (2006.01)
*C07F 15/00* (2006.01)
*H05B 33/14* (2006.01)
*H01L 51/50* (2006.01)

(52) U.S. Cl.
CPC ........ *H01L 51/0087* (2013.01); *C07F 15/0066* (2013.01); *C07F 15/0093* (2013.01); *C09K 11/06* (2013.01); *H05B 33/14* (2013.01); *C09K 2211/185* (2013.01); *H01L 51/0081* (2013.01); *H01L 51/0094* (2013.01); *H01L 51/5016* (2013.01); *Y02E 10/549* (2013.01)

(58) Field of Classification Search
CPC ............ H01L 51/0084; H01L 51/0085; H01L 51/0087; H01L 51/0091; H01L 51/502; H05B 33/14; C09K 11/06; C09K 2211/06; C07F 1/00; C07F 15/0006; C07F 15/0033; C07F 15/006; C07F 15/0073; C07F 15/0086
See application file for complete search history.

(56) References Cited

U.S. PATENT DOCUMENTS

| 6,137,118 A * | 10/2000 | Kunugi et al. ............ 257/40 |
| 6,984,591 B1 | 1/2006 | Buchanan et al. |
| 2001/0030508 A1* | 10/2001 | Utsugi et al. ............ 313/505 |
| 2002/0034656 A1* | 3/2002 | Thompson et al. .......... 428/690 |
| 2002/0042174 A1* | 4/2002 | Kunugi et al. ............ 438/199 |
| 2002/0179885 A1 | 12/2002 | Che et al. |
| 2002/0193532 A1* | 12/2002 | Ikehira et al. ............ 525/333.3 |
| 2003/0091862 A1* | 5/2003 | Tokito et al. ............ 428/690 |
| 2003/0186080 A1 | 10/2003 | Kamatani et al. |
| 2003/0205707 A1 | 11/2003 | Chi-Ming |
| 2004/0183082 A1 | 9/2004 | Yamazaki |
| 2005/0020449 A1 | 1/2005 | Blais |
| 2007/0111025 A1* | 5/2007 | Lennartz et al. ............ 428/690 |
| 2007/0135635 A1 | 6/2007 | Stossel et al. |
| 2007/0264524 A1 | 11/2007 | Gessner et al. |
| 2011/0049501 A1 | 3/2011 | Bold et al. |

FOREIGN PATENT DOCUMENTS

| DE | 10338550 A1 | 3/2005 |
| DE | 10350606 A1 | 6/2005 |
| DE | 10358665 A1 | 7/2005 |
| EP | 1703572 A1 | 9/2006 |
| JP | 2002-241751 A | 8/2002 |
| JP | 2004-281274 A | 10/2004 |
| JP | 2005-276581 A | 6/2005 |
| WO | WO-03/095587 A1 | 11/2003 |
| WO | WO-2004/016711 A1 | 2/2004 |
| WO | WO-2004017043 A3 | 6/2004 |
| WO | WO 2005/056712 A1 * | 6/2005 ............. C09K 11/06 |
| WO | WO-2005/098988 A1 | 10/2005 |

OTHER PUBLICATIONS

Sun et al. "Luminescent one-dimensional nanoscale materials with PtII . . . PtII interactions." Angew. Chem. Int. Ed. 2006. vol. 45, pp. 5610-5613.*
Adachi et al., "High-efficiency red electrophosphorescnce devices", Applied Physics Letters, vol. 78, No. 11, (2001), pp. 1622-1624.
Bois et al., "Structural studies of [Pt(CNMe)4][M(mnt)2]n {M = Pd or Pt, mnt = [S2C2(CN)2]2-, n= 1 or 2}: structure-dependent paramagnetism of three crystal forms of {Pt(CNME)4] [Pt(mnt)2]2", J. Chem. Soc., (1998), pp. 2833-2838.
Bonati et al., "New Isocyanide Complexes of Platinum (II)", Journal of Organometallic Chemistry, Vo. 24, (1970), pp. 251-256.
Buss et al., "Structural Investigations of Vapochromic Behavior. X-ray Single-Crystal and Powder Diffraction Studies of [Pt(CN-iso-C3H7)4][M(CN)4] fr M = Pt or Pd", J. Am. Chem. Soc., vol. 120, No. 31, (1998), pp. 7783-7790.
Buss et al., "Synthesis and Characterization of Pt(CN-p-(CH)CH) (CN), a Crystalline Vapoluminescent Compound That Detects Vapor-Phase Aromatic Hydrocarbons", J. Am. Chem., vol. 124, No. 6, (2002), pp. 1031-1039.
Gitzel et al., "Physical Properties of Crystallized Dichloro(bis-isonitrile)platinum(II) complexes", vol. 28b, (1973), pp. 161-163.
Guo et al., "Transition metal complexes of isocyanopyridines, isocyanoquinolines and isocyanoisoquinolines", Inorganica Chimica Acta, vol. 261, (1997), pp. 141-146.

(Continued)

*Primary Examiner* — Michael H Wilson
(74) *Attorney, Agent, or Firm* — Drinker Biddle & Reath LLP

(57) ABSTRACT

The present invention relates to light-emitting devices and in particular organic light-emitting devices (OLEDs). In particular, the invention relates to the use of luminescent isonitrile/metal complexes as oligomer emitters in devices of this type.

20 Claims, 17 Drawing Sheets

(56) References Cited

OTHER PUBLICATIONS

Isci et al., "Electronic structure and spectra of square-planar alkyl isocyanide complexes", *Inorganic Chemistry*, vol. 14, No. 4, (1975), pp. 913-918.
Isci et al., "Anion-cation interaction in tetrakis(alkylisocyanide) platinum (II) tetracyanoplatinato(II) double complexes in the solid state and in solution", *Inorg. Chem.*, vol. 13, No. 5, (1974), pp. 1175-1180.
Keller et al., "Characterization of Tetrakis(isonitrile) platinum(II)-tetrachloroplatinates(II), [Pt(CNR)4][PtC14]", *Ionic Isonitrile Complexes*, vol. 31b, (1976), pp. 565-568.
Keller et al., "Chemical and Physical Properties of Dichloro-bis(isocyanide)-platinum(II) Co-ordination Compounds with Columnar Structure", *Z. Naturforsch*, vol. 27b, (1972), pp. 631-634.
Okada et al., "Sustituent effects of iridium complexes for highly effiecient red OLEDs", *Dalton Trans.*, (2005), pp. 1583-1590.
Ren et al., "Ultrahigh Energy Gap Hosts in Deep Blue Organic Electrophosphorescent Devices", *Chem Mater.*, vol. 16, No. 23, (2004), pp. 4743-4747.
Shinar, J., "Organic Light-Emitting Devices—A Survey", AIP-Press, (2004), pp. 9-10, pp. 23-29.
Sotoyama et al., "Efficient organic light-emitting diodes with phosphorescent platinum complexes contaning NCN—coordinating tridentate ligand", *Applied Physics Letters*, vol. 86, (2005), pp. 153505-153505-3.
Tang et al., "Organic electroluminescent diodes", *Appl. Physics Lett.*, vol. 51, (1987), pp. 913-915.
Tung et al., "Organic light-emitting diodes based on charge-neutral Os(II) emitters: generation of saturated red emission with very high external quantum efficiency", *Journal of Materials Chemistry*, vol. 15, (2005), pp. 460-464.
Ungváry et al., "Effect of Solvent Viscosity on the Reaction of Styrenes With HCo(CO)4 and CO", *Journal of Organometallic Chemistry*, vol. 249, (1983), pp. 411-414.
Winzeburg et al., "Rhodium and Platinum(II) Complexes With Chelating Bidentate Isonitrile Ligands", *Journal of Organometallic Chemistry*, vol. 249, (1983), pp. 415-428.
Yang et al., "Polymer electrophosphorescence devices with high power conversion efficiencies", *Applied Physics Letters*, vol. 84, No. 14, (2004), pp. 2476-2478.
Yersin, H., "Triplet Emitters for OLED Applications. Mechanisms of Exciton Trapping and Control of Emission Properties", *Top Curr Chem*, vol. 241, (2004), pp. 1-26.
Connelly et al., "New Linear Chain Mixed Metal Compounds: Complex Salts of [Pt(CNMe)4]2=", *J. Chem. Soc.*, (1992), pp. 1564.
Daws et al., "Vapochromic Compounds as Environmental Sensors. 2. Synthesis and Near-Infrared and Infrared Spectrocscopy Studies of [Pt(arylisocyanide)] [Pt(CN)] upon Exposure to Volatile Organic Compound Vapors", *Chemistry of Materials*, vol. 9, No. 1, (1997), pp. 363-368.
Drew et al., "An Electronic Nose Transducer Array of Vapoluminescent Platinum(II) Double Salts", *Journal of the American Chemical Society*, vol. 123, No. 34, (2001), pp. 8414-8415.
Exstrom et al., "Inclusion of Organic Vapors by Crystalline, Solvatochromic [Pt(aryl isonitrile)4] [Pd(CN)4] Compounds. "Vapochromic" Environmental Sensors", *Chemistry of Materials*, vol. 7, No. 1, (1995), pp. 15-17.
Keller et al., "A Phenylisonitrileplatinum(II) Compound of Stoichiometry Pt(CN)2 (CNC6H5)", *Inorg. Nucl. Chem.*, vol. 11, (1975), pp. 765-768.
Martellaro et al., "Multinuclear nuclear magnetic resonance and X-ray crystallographic investigation of some mixed ligand alkylisocyanide platinum(II) complexes", *Inorg. Chim. Acta.*, vol. 358, (2005), pp. 3377-3383.
Martellaro at al., "Solution Equilibria of Tetrakis (ethyisocyanide) platinum(II) with Tetracyanoplatinate(II): Equilibria and Thermodynamics of the Formation of Di-, Tri-, and Tetraplatinum Species", *Inorganic Chemistry*, vol. 39, No. 9, (2000), pp. 1878-1881.
Mason et al., "Electronic structures of square-planar complexes", *J. Am. Soc.*, vol. 90, No. 21, (1968), pp. 5721-5729.
Miller at al., "Preparation and reactions of tetrakis(methyl isocyanide) complexes of divalent nickel, palladium, and platinum", *Inorganic Chemistry*, vol. 11, No. 9, (1972), pp. 2069-2074.
Pawloskski et al., "Synthesis, Structure, Optical Properties and Theoretical Studies of Pt(P-P)(CN)2 with P-P = 1,2 Bis(diphenylphosphanyl) benzene and 2,2 -Bis (diphenylphosphany)- 1,1 binaphthyl—Luminescence from Metal-to-Ligand Charge Transfer and Intraligand States", *Er. J. Inorg. Chem.*, (2004), pp. 4242-4246.
Treichel et al., "New isocyanide-platinum complexes", *Journal of the American Chemical Society*, vol. 93, No. 21, (1971), pp. 5424-5433.
Decision to Dismiss the Amendment from corresponding Japanese Patent Application No. 2009-517031 dated Jul. 8, 2014.

* cited by examiner

Figure 1

| | |
|---|---|
| Cathode: Al | 200 nm |
| Interlayer: LiF | 0.8 nm |
| Electron-conduction layer ETL: Alq$_3$ | 40 nm |
| Emitter layer EML: UGH with 30% complex doping | 30 nm |
| Hole-transport layer HTL: α-NPD | 30 nm |
| Hole-injection layer HIL: CuPc | 10 nm |
| Anode ITO | 40 nm |
| Support material glass | |

Alq$_3$ = aluminium 8-hydroxyquinoline
α-NPD = 4,4'-bis[N-(1-naphthyl)-N-phenylamino]biphenyl
CuPc = copper phthalocyanine
UGH is an "ultrahigh energy gap host" matrix material having a high singlet S$_0$ – triplet T$_1$ energy gap for blue or white electroluminescence. UGH 2 (= p-bis(triphenylsilyl)-benzene) or UGH 3 (= m-bis(triphenylsilyl)benzene) is preferred
ITO = indium tin oxide

Figure 3

| |
|---|
| Cathode, Al: |
| Interlayer CsF: 0.8 nm |
| ETL, $Alq_3$: 40 nm |
| Emitter layer: 10 to 80 nm |
| HTL, PEDOT: PSS: 50 nm |
| Anode, ITO: 40 nm |
| Support material, glass |

(Mass spectrum is available)

OLIGOMERS OF ISONITRILE-METAL COMPLEXES AS TRIPLET EMITTERS FOR OLED APPLICATIONS

The present invention relates to light-emitting devices and in particular organic light-emitting devices (OLEDs). In particular, the invention relates to the use of luminescent isonitrile/metal complexes as oligomer emitters in devices of this type.

OLEDs (organic light-emitting devices or organic light-emitting diodes) represent a new technology which will dramatically change display-screen and lighting technology. OLEDs consist predominantly of organic layers, which can also be manufactured to be flexible and inexpensively. OLED components can be designed with large areas as lighting units, but also in small form as pixels for displays.

An overview of the functioning of OLEDs is given, for example, in H. Yersin, Top. Curr. Chem. 2004, 241, 1.

The functioning of OLEDs has also been described in C. Adachi et al., Appl. Phys. Lett. 2001, 78, 1622; X. H. Yang et al., Appl. Phys. Lett. 2004, 84, 2476; J. Shinar, "Organic Light-Emitting Devices—A Survey", AIP-Press, Springer, New York 2004; W. Sotoyama et al., Appl. Phys. Lett. 2005, 86, 153505; S. Okada et al., Dalton Trans., 2005, 1583, and Y.-L. Tung et al., J. Mater. Chem., 2005, 15, 460-464.

Since the first reports of OLEDs (see, for example, Tang et al., Appl. Phys. Lett. 1987, 51, 913), these devices have been developed further, in particular with respect to the emitter materials employed, where so-called triplet or phosphorescent emitters are of particular interest.

Compared with conventional technologies, such as, for example, liquid-crystal displays (LCDs), plasma displays or cathode-ray tubes (CRTs), OLEDs have numerous advantages, such as, for example, a low operating voltage, a flat design, highly efficiently self-illuminating pixels, high contrast and good resolution, as well as the possibility of displaying all colours. Furthermore, an OLED emits light on application of an electrical voltage instead of only modulating it. Whereas numerous applications have already been developed for OLEDs and novel areas of application have also been opened up, there is still a demand for improved OLEDs and in particular for improved triplet emitter materials. In particular, problems with the long-term stability, thermal stability and chemical stability to water and oxygen occur in the solutions to date. Furthermore, many emitters exhibit only low sublimability. Furthermore, important emission colours are often not available with emitter materials known to date. same time as high current densities or high luminous densities. Finally, problems exist with respect to manufacturing reproducibility in the case of many emitter materials.

In conventional OLED arrangements, emitter molecules are present in the emitter layer in a usual doping concentration of about 5%. For example, the charge carriers recombine at the emitter molecules and result in excited states of the emitter molecules. The excited states then release their energy as light emission. The use of a higher emitter molecule concentration could in principle result in significantly higher efficiency at high current densities. However, this is hindered by the fact that adjacent emitter molecules then generally undergo interactions, for example triplet-triplet annihilations or a self-quenching process. This results in a limitation of the usual maximum usable concentration of the emitter molecules in the emitter layer. It would therefore be favourable to be able to provide emitter molecules in the case of which a self-quenching process does not occur, even in the case of high concentrations in the emitter layer.

It has furthermore been observed that the light yield for OLEDs comprising organometallic substances, so-called triplet emitters, can be significantly greater than for purely organic materials. Owing to this property, the further development of organometallic materials is of essential importance. Triplet emitters are described, for example, in WO 2004/017043 A2 (Thompson), WO 2004/016711 A1 (Thompson), WO 03/095587 (Tsuboyama), US 2003/0205707 (Chi-Ming Che), US 2002/0179885 (Chi-Ming Che), US 2003/186080 A1 (J. Kamatani), DE 103 50 606 A1 (Stößel), DE 103 38 550 (Bold), DE 103 58 665 A1 (Lennartz).

It was an object of the present invention to provide novel emitter materials, in particular for OLEDs, and novel light-emitting devices which at least partially overcome the disadvantages of the prior art and which enable, in particular, a high doping concentration.

This object is achieved in accordance with the invention by a light-emitting device comprising (i) an anode, (ii) a cathode and (iii) an emitter layer, arranged between and in direct or indirect contact with the anode and cathode, comprising at least one complex of the formula (I)

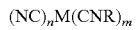  formula I in which
M represents Pt(II), Rh(I), Ir(I), Pd(II) or Au(III), in particular Pt(II) or Pd(II),
R on each occurrence, independently of one another, represents a hydrocarbon group, which may optionally contain heteroatoms,
n=0 to 4
and
m=0 to 4, where the proportion of complexes of the formula (I) in the emitter layer is more than 10% by weight, based on the total weight of the emitter layer. Preferably, m=4−n, so that the complexes are tetracoordinated, in particular planar complexes.

Surprisingly, it has been found that the use according to the invention of the complexes of the formula (I) in the emitter layer enables light-emitting devices to be obtained which have excellent properties. In particular, the compounds employed in accordance with the invention exhibit high quantum yields. In addition, the complexes can be varied by substitution and/or modification of the ligands, giving rise to a wide variety of possibilities for the modification or control of the emission properties. In addition, compounds having good sublimability can be obtained through a suitable choice of the ligands, in particular through the use of F-containing groups R.

The invention preferably relates to an organic light-emitting device (OLED).

The way in which an embodiment of the light-emitting devices according to the invention functions is shown diagrammatically in FIG. 1. The device comprises at least an anode, a cathode and an emitter layer. One or both of the electrodes used as cathode or anode advantageously have a transparent design, enabling the light to be emitted through this electrode. The transparent electrode material used is preferably indium tin oxide (ITO). A transparent anode is particularly preferably employed. The other electrode can likewise be made of a transparent material, but may also be formed from another material having a suitable electron work function if light is only to be emitted through one of the two electrodes. The second electrode, in particular the cathode, preferably consists of a metal of high electrical conductivity, for example aluminium or silver, or an Mg/Ag or Ca/Ag alloy. An emitter layer is arranged between the two electrodes. This can be in direct contact or indirect contact with the anode and cathode, where indirect contact means that further layers are present between the cathode or anode and the emitter layer, so that the emitter layer and the anode and/or cathode do not touch one another, but instead are in electrical contact with one another via further interlayers. On application of a voltage, for example a voltage of 2-20 V, in particular 5-10 V, negatively charged electrons are emitted from the cathode, for example a conductive metal layer, particularly preferably from an aluminium cathode, and migrate in the direction of the positive anode. Positive charge carriers, so-called holes, in turn migrate from this anode in the direction of the cathode. In accordance with the invention, the emitter layer arranged between the cathode and anode comprises oligomers of the organometallic complexes of the formula (I) as emitters. The migrating charge carriers, i.e. a negatively charged electron and a positively charged hole, recombine at the emitter oligomers or in their vicinity and result in neutral, but energetically excited states of the emitter molecules. The excited states of the emitter molecules then release the energy as light emission.

The light-emitting devices according to the invention can be produced by vacuum deposition so long as the emitter materials are sublimable. Alternatively, build-up via wet-chemical application is also possible, for example via spin-coating methods, via ink-jet printing or via screen-printing methods. It is also possible to apply emitter materials as colloidal suspensions. This is advantageous, in particular, in the case of oligomer materials according to the invention having low solubility. The structure of OLED devices is described in detail, for example, in US 2005/0260449 A1 and in WO 2005/098988 A1.

The light-emitting devices according to the invention can be manufactured by means of the vacuum sublimation technique and comprise a plurality of further layers, in particular an electron-injection layer and an electron-conduction layer (for example $Alq_3$=Al 8-hydroxyquinoline or Alq=Al bis(2-methyl-8-hydroxyquinolato)-4-phenylphenolate) and/or a hole-injection (for example CuPc) and hole-conduction layer or hole-conduction layer (for example α-NPD). However, it is also possible for the emitter layer to take on functions of the hole- or electron-conduction layer.

The emitter layer preferably consists of an organic matrix material having a sufficiently large singlet $S_0$-triplet $T_1$ energy gap (UGH matrix material), for example comprising UGH, PVK (polyvinylcarbazole), CBP (4,4'-bis(9-carbazolyl)biphenyl) or other matrix materials. The emitter complex is doped into this matrix material in a high concentration, for example preferably to the extent of 10 to 30 percent by weight.

The emitter layer can also be achieved without a matrix by applying the corresponding complex as 100% material. A corresponding embodiment is described below.

In a particularly preferred embodiment, the light-emitting device according to the invention also has a CsF or LiF interlayer between the cathode and the emitter layer or an electron-conductor layer. This layer has, in particular, a thickness of 0.5 nm to 2 nm, preferably about 1 nm. This interlayer predominantly causes a reduction in the electron work function.

The light-emitting device is furthermore preferably applied to a substrate, for example to a glass substrate.

In a particularly preferred embodiment, an OLED structure for a sublimable emitter according to the invention also comprises, besides an anode, emitter layer and cathode, at least one, in particular a plurality of and particularly preferably all the layers mentioned below and shown in FIG. 2.

The entire structure is preferably located on a support material, where, in particular, glass or any other solid or flexible transparent material can be employed for this purpose. The anode, for example an indium tin oxide (ITO) anode, is arranged on the support material. A hole-transport layer (HTL), for example α-NPD (N,N'-diphenyl-N,N'-bis (1-methyl)-1,1'-biphenyl-4,4'-diamine), is arranged on the anode and between the emitter layer and the anode. The thickness of the hole-transport layer is preferably 10 to 100 nm, in particular 30 to 50 nm. Further layers which improve hole injection, for example a copper phthalocyanine (CuPc) layer, may be arranged between the anode and the hole-transport layer. This further layer preferably has a thickness of 5 to 50 nm, in particular 8 to 15 nm. An electron-blocking layer, which ensures that electron transport to the anode is suppressed since a current of this type would only cause ohmic losses, is preferably applied to the hole-transport layer and between the hole-transport layer and the emitter layer. The thickness of this electron-blocking layer is preferably 10 to 100 nm, in particular 20 to 40 nm. This additional layer can be omitted, in particular, if the HTL layer is already intrinsically a poor electron conductor.

The next layer is the emitter layer, which comprises or consists of the emitter material according to the invention. In the embodiment using sublimable emitters, the emitter materials are preferably applied by sublimation. The layer thickness is preferably between 10 nm and 200 nm, in particular between 50 nm and 150 nm. The emitter material according to the invention may also be co-evaporated together with other materials, in particular with matrix materials. For emitter materials according to the invention which emit in the green or red, common matrix materials such as CBP (4,4'-bis(N-carbazolyl)biphenyl). However, it is also possible to construct a 100% emitter material layer. For emitter materials according to the invention which emit in the blue, UGH matrix materials are preferably employed (cf. M. E. Thompson et al., Chem. Mater. 2004, 16, 4743), Co-evaporation can likewise be used to generate light of mixed colour on use of compounds according to the invention with different metal central ions. For example, co-evaporation can be carried out in order to generate white or blue light on use of Pd compounds with low doping by Pt compounds.

A hole-blocking layer, which reduces ohmic losses which could arise due to hole currents to the cathode, is preferably applied to the emitter layer. This hole-blocking layer preferably has a thickness of 10 to 50 nm, in particular 15 to 25 nm. A suitable material for this purpose is, for example, BCP (4,7-diphenyl-2,9-dimethylphenanthroline, also known as bathocuproin). An ETL layer comprising electron-transport material (ETL=electron-transport layer) is preferably applied to the hole-blocking layer and between this layer and the cathode. This layer preferably consists of vapour-depositable $Alq_3$ having a thickness of 10 to 100 nm, in particular 30 to 50 nm. An interlayer, for example comprising CsF or LiF, is preferably applied between the ETL layer and the cathode. This interlayer reduces the electron-injection barrier and protects the ETL layer. This layer is generally applied by vapour deposition. The interlayer is preferably very thin, in particular having a thickness of 0.5 to 5 nm, more preferably 0.5 to 2 nm. Finally, a conductive cathode layer is also applied by vapour deposition, in particular having a thickness of 50 to 500 nm, more preferably 100 to 250 nm. The cathode layer preferably consists of Al, Mg/Ag (in particular in the ratio 10:1) or other metals. Voltages of between 3 and 15 V are preferably applied to the OLED structure described for a sublimable emitter according to the invention.

The OLED device can also be manufactured in part by wet-chemical methods, for example with the following structure: glass substrate, transparent ITO layer (comprising indium tin oxide), for example PEDOT/PSS (for example 40 nm), 100% complex according to the invention (for example 10 to 80 nm) or doped (for example 30%, in particular 10% to 40%) into a suitable matrix (for example 40 nm), vapour-deposited Alq$_3$ (for example 40 nm), vapour-deposited LiF or CsF as protective layer (for example 0.8 nm), vapour-deposited metal cathode Al or Ag or Mg/Ag (for example 200 nm).

An OLED structure for a soluble emitter according to the invention particularly preferably has the structure described below and shown in FIG. 3, but comprises at least one, more preferably at least two and most preferably all the layers mentioned below.

The device is preferably applied to a support material, in particular to glass or another solid or flexible transparent material. An anode, for example an indium tin oxide anode, is applied to the support material. The layer thickness of the anode is preferably 10 nm to 100 nm, in particular 30 to 50 nm. An HTL layer comprising a hole-conductor material, in particular comprising a water-soluble hole-conductor material, is applied to the anode and between the anode and the emitter layer. A hole-conductor material of this type is, for example, PEDOT/PSS (polyethylenedioxythiophene/polystyrene-sulfonic acid). The layer thickness of the HTL layer is preferably 10 to 100 nm, in particular 40 to 60 nm. The emitter layer (EML) which comprises a soluble emitter according to the invention is applied next. The material can be dissolved in a solvent, for example in acetone, dichloromethane or acetonitrile. This may prevent dissolution of the underlying PEDOT/PSS layer. The emitter material according to the invention can be employed in a moderate concentration, for example 20% by weight, but also in a higher concentration or as a 100% layer. It is also possible to apply the emitter material highly or moderately doped in a suitable polymer layer (for example PVK=polyvinylcarbazole). The doping concentration should be selected to be sufficiently high that dimerisation, trimerisation or oligomerisation of the emitter can take place.

For low-solubility emitter materials according to the invention, application by means of a colloidal suspension in a polymer can be carried out. Oligomer strands can be comminuted with ultrasound treatment before introduction into the polymer and introduced into the polymer after filtering through nanofilters. The emitter layer preferably has a layer thickness of 10 to 80 nm, in particular 20 to 60 nm.

A layer of electron-transport material is preferably applied to the emitter layer, in particular with a layer thickness of 10 to 80 nm, more preferably 30 to 50 nm. A suitable material for the electron-transport material layer is, for example, Alq$_3$, which can be applied by vapour deposition. A thin interlayer which reduces the electron-injection barrier and protects the ETL layer is preferably applied next. This layer preferably has a thickness of between 0.5 and 2 nm, in particular between 0.5 and 1.0 nm, and preferably consists of CsF or LiF. This layer is generally applied by vapour deposition. For a further-simplified OLED structure, the ETL layer and/or the interlayer may optionally be omitted.

Finally, a conductive cathode layer is applied, in particular by vapour deposition. The cathode layer preferably consists of a metal, in particular Al or Mg/Ag (in particular in the ratio 10:1).

Voltages of 3 to 15 V are preferably applied to the device.

The light-emitting device according to the invention is preferably insulated or encapsulated from the environment, in particular insulated in a gas-tight manner. Gas exchange with the environment and ingress or introduction of gas from the environment into the emitter layer are thereby prevented. The layer composition thereby remains constant, which results in the same colour being emitted constantly. In particular, the device according to the invention is designed in such a way that absolutely no material exchange and in particular also no solvent vapour exchange takes place with the environment.

It is essential to the invention that the light-emitting device comprises at least one isonitrile/complex material of the formula (I) as emitter.

Isonitriles, as organic homologues of the cyanides, are a widespread class of ligands. Platinum/isonitrile complexes exist, inter alia, as neutral complex compounds [cis-Pt(CN)$_2$(CNR)$_2$]. They are readily soluble in polar organic solvents and exhibit a wide variety of spectroscopic phenomena in the solid state, which are ultimately attributable to the columnar structure. Isonitrile complexes and uses thereof to date are described, for example, in L. Ramberg, Chem. Ber. 1907, 40, 2578; K. A. Hofmann, G. Bugge, Chem. Ber. 1907, 40, 1772; L. Tschugaeff et al., Chem. Ber. 1914, 47, 568; F. Bonati et al., J. Organomet. Chem. 1970, 24, 251; H. Bois et al., J. Chem. Soc., Dalton Trans. 1998, 2833; M. L. Winzenburg et al., J. Organomet. Chem. 1983, 249, 414; C. E. Buss et al., J. Am. Chem. Soc. 2002, 124, 1031; H. Isci et al., Inorg. Chem. 1975, 14, 1175; H. Isci et al., Inorg. Chem. 1975, 14, 913; H. J. Keller et al., Inorg. Nucl. Chem. Letters 1975, 11, 765; H. J. Keller et al., Z. Naturforsch. 1972, 27b, 631; H. J. Keller et al., Z. Naturforsch. 1976, 31b, 565; C. E. Buss et al., J. Am. Chem. Soc. 1998, 120, 7783; J. Guo et al., Inorg. Chim. Acta 1997, 261, 141; P. J. Martellaro et al., Inorg. Chem. 2000, 39, 1878; J. S. Miller et al., Inorg. Chem. 1972, 11, 2069; N. G. Connelly et al., J. Chem. Soc., Dalton Trans. 1992, 1564; P. M. Treichel et al., J. Am. Chem. Soc. 1971, 93, 5424; L. Tschugaeff et al., Chem. Ber. 1914, 47, 2643; C. A. Daws et al., Chem. Mater. 1997, 9, 363; C. L. Exstrom et al., Chem. Mater. 1995, 7, 15; S. M. Drew et al., J. Am. Chem. Soc. 2001, 123, 8414; US 006137118A.

It has now surprisingly been observed in accordance with the invention that compounds of the formula (I) are eminently suitable as emitter molecules for light-emitting devices and in particular for organic light-emitting devices (OLEDs). The compounds according to the invention are eminently suitable, in particular, for use in light-generating systems, such as, for example, displays or lighting.

The use of the substances according to the invention in or as emitter layers of OLEDs makes it possible to use for light emission an emission process which has hitherto not been used. The transitions which result in emission are, in the case of this class of compounds, based on metal-metal interactions between adjacent complexes. This represents a major difference from previous systems, in which the light emission is based on the emission from isolated monomeric molecules. In the known OLED systems, the concentration of the emitter molecules in the emitter layer was always kept low, since quenching was observed at relatively high concentrations in the case of conventional monomer emitters. By contrast, the emitters are, in accordance with the invention, introduced into the emitter layer in a high concentration of >10% by weight, based on the total weight of the emitter layer. Adjacent complexes are consequently sufficiently close to one another in order to enable emission based on M-M interactions to take place.

Depending on the doping amount and depending on the radicals R, the compounds according to the invention have different M-M separations in the emitter layers. The emission colours can thus be changed over broad ranges. Emission energy shifts into the red with decreasing separation.

The use of isonitrile/metal complexes of the formula (I) as emitter materials in OLEDs gives rise to a number of advantages. Thus, for example, highly concentrated emitter layers having a proportion of emitter of up to 100% can be produced by sublimation or by deposition from solution. In the case of 100% emitter layers, concentration variations cannot occur during manufacture of the devices. It is furthermore possible to provide the emitter in crystalline or quasi-crystalline layers or in oligomer layers. In these systems, in particular in crystalline layers, the charge-carrier mobilities are significantly higher than in amorphous layers and therefore prove to be particularly favourable for achieving low operating voltages and balanced charge-carrier balances. Furthermore, high luminous densities can be achieved at the same time as high current densities with the emitter molecules according to the invention. In addition, relatively high efficiency (quantum efficiency) can also be achieved at high current densities.

The emitter-oligomer units employed in accordance with the invention are the complexes of the formula (I) $(NC)_nM(CNR)_m$. In the case of oligomers of these complexes, the systems are, in particular, luminescent systems. The complexes have a central atom, which is selected from Pt, Pd, Rh, Ir and Au, in particular Pt and Pd. The central atom is preferably in the form of Pt(II), Pd(II), Rh(I), Ir(I) or Au(III), i.e. a singly or doubly or triply positively charged ion. The central atom is particularly preferably Pt(II) or Pd(II). In accordance with the invention, the central atom is tetracoordinated.

Furthermore, the complex employed in accordance with the invention contains groups CN or CNR, i.e. m+n≠0 and in particular m+n≥1, more preferably m+n≥2, still more preferably m+n≥3 and in particular m+n≤8, preferably m+n≤6. m and n here are preferably integers. m is furthermore preferably at least 1. n+m is particularly preferably=4. Most preferably, in particular for Pt(II) and Pd(II), n=m=2.

The radical R here represents a hydrocarbon group, which may optionally contain heteroatoms. The heteroatoms are selected, in particular, from O, S, N, P, Si, Se, F, Cl, Br and/or I. The radicals R preferably contain 0 to 50, in particular 0 to 10 and still more preferably 0 to 5, heteroatoms. The heteroatoms here can be in the skeleton or part of substituents. In an embodiment, the radical R is a hydrocarbon group which contains one or more functional groups. Suitable functional groups are, for example, halogen, in particular F, Cl, Br or I, alkyl, in particular $C_1$ to $C_{20}$, still more preferably $C_1$ to $C_6$ aryl, O-alkyl, O-aryl, S-aryl, S-alkyl, P-alkyl$_2$, P-aryl$_2$, N-alkyl$_2$ or N-aryl$_2$. In many cases, it is preferred for the radical R to contain at least one fluorine in order to increase the volatility of the complex. In particular, the hydrocarbon group R is an alkyl, alkenyl, alkynyl, aryl or heteroaryl group. In a further preferred embodiment, the group R=SO$_2$R', where R' in turn represents a hydrocarbon group, which may contain one or more heteroatoms. R' is preferably alkyl, aryl, heteroaryl, which may optionally contain one or more functional groups, as indicated above. Complexes according to the invention and in particular complexes where M=Pt, in which R in each case represents an aliphatic radical, are preferred. R here is, in particular, a saturated hydrocarbon radical, in particular having 1 to 30 C atoms, preferably having 2 to 20 C atoms, which may optionally contain heteroatoms. Substituents R of different sizes enable different emission colours to be obtained by variation of the M-M separations, for example blue-green to orange. The radicals may contain substituents in order to increase the variability. Preferred substituents are F, CF$_3$, OCH$_3$, OC$_2$H$_5$ and N(CH$_3$)$_2$.

Preference is furthermore given to complexes, in particular where M=Pt, in which the radical R in each case contains an aromatic group. Compounds of this type advantageously enable, for example, emission in the red region to be obtained.

However, it is also possible for two groups CNR together in the complexes according to the invention to form a bridging ligand CN—R''—NC, where R'' then represents a linking group analogously to the meanings indicated above for R. R'' is preferably an alkylene, alkenylene, alkynylene, arylene or heteroarylene radical, which may optionally contain heteroatoms.

Unless indicated otherwise, the term alkyl or alk, as used herein, in each case independently signifies a $C_1$-$C_{20}$, in particular a $C_1$-$C_6$ hydrocarbon group. The term aryl signifies an aromatic system having 5 to, for example, 20 C atoms, in particular having 6 to 10 C atoms, where C atoms may optionally be replaced by heteroatoms (for example N, S, O) (also referred to herein as heteroaryl).

The compounds of the formula (I) according to the invention are preferably neutral complexes.

In a further preferred embodiment, the complex of the formula (I) $(NC)_nM(CNR)_m$ present in accordance with the invention in the emitter layer represents a complex of the formula (II)

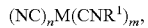
$(NC)_nM(CNR^1)_m,$ formula II, where $R^1$ represents a radical which contains a polymerisable group. The radical $R^1$ is, in particular, a radical R which (additionally) contains a polymerisable group, for example a C=C double-bond group.

The complex of the formula (I) here can be fixed to a polymer by functionalisation of the ligand $R^1$ by means of a polymerisable group. The complex is thus immobilised, so that crystallisation of the emitter, which is unwanted in another use, in the emitter layer, which is frequently a reason for a limited lifetime of OLEDs, is prevented. In this embodiment, the complex of the formula (I) in the emitter layer is bonded to a polymer via the polymerisable ligand. The bonding to a polymer enables a homogeneous distribution of the emitter in the emitter layer and in addition reliable control of the complex content to be achieved.

In order to provide the light-emitting devices according to the invention, the polymer which contains bonded $(NC)_nM(CNR^1)_m$ groups can firstly be prepared and then applied, for example as a solution by means of spin coating or ink-jet printing. However, it is also possible for the monomer to be applied and polymerised on site. Suitable radicals $R^1$ include, for example, the radicals R indicated above which additionally contain a radical which is polymerisable, for example a C=C radical. The radicals $R^1$ are particularly preferably —CH=CH$_2$, —CH$_2$—CH=CH$_2$ or —CH$_2$—C$_6$H$_4$—CH=CH$_2$. It is important that the complexes are present in a sufficiently high concentration in order to enable an M-M interaction.

Examples of polymerisable functions of this type which contain the group $R^1$ are, for example, olefin groups, in particular vinyl groups, epoxides or cyclic ethers for polymerisation reactions, cyanates or alcohols for polyaddition reactions, carboxylates and amines or alcohols for polycondensation reactions and aryl halides and organoboronic acid or halide and olefin for coupling reactions.

It has been found in accordance with the invention that excellent emitter layers can be obtained in the case of high doping of the layers with the complexes of the formula (I).

The emitter layer comprises complexes of the formula (I) in a concentration of >10% by weight, based on the total weight of the emitter layer, in particular >20% by weight, preferably >30% by weight, more preferably >50% by weight, in particular >80% by weight and most preferably >90% by weight. However, it is also possible to provide emitter layers which consist virtually completely of complexes of the formula (I) and in particular comprise >95% by weight, more preferably >99% by weight. In a further embodiment, the emitter layer consists completely, i.e. to the extent of 100%, of complexes of the formula (I). On use of the complexes according to the invention in a high concentration in the emitter layer, crystalline layers or stacks of the complexes and in particular columnar structures having relatively short metal-metal separations form. Stacks of this type are formed, in particular, in the case of planar complexes and particularly favourably in the case of planar platinum complexes and palladium complexes. Strong electronic interactions, which result in a characteristic emission behaviour, occur in these stacks. The emission wavelength here is determined predominantly by the M-M separation and can be determined in a simple manner by the group R. The use of highly concentrated emitter layers and in particular crystalline or quasi-crystalline layers offers considerable advantages. In particular, no concentration variations occur during manufacture or these have only a small effect in highly concentrated systems. Furthermore, the charge-carrier mobilities, i.e. the electron or hole mobilities, are significantly higher in the case of the formation of crystalline layers than in amorphous layers. Furthermore, a high luminous density and high efficiency, i.e. high quantum efficiency, can be achieved with concentrated emitter layers of this type at high current to densities. The emitter complexes employed in accordance with the invention have extremely intense emission with a high emission quantum yield predominantly through metal-metal interactions between the central atoms of the individual complexes, in particular owing to metal-metal interactions between planar metal complexes. The emission is thus caused by the interaction of the complexes present in a high concentration. In contrast to materials of the prior art, emitter layers having a high proportion of emitter molecules as well as emitter layers comprising uniform units having a crystalline or quasi-crystalline order can thus be provided. To date, the use of emitter molecules from the prior art in high concentrations has not resulted in highly efficient emitter layers since, in particular, an electronic interaction of adjacent emitter molecules has resulted in self-quenching effects. This had the consequence that the emission quantum yield drops significantly with increasing concentration of the emitter molecules, in particular from a concentration of >10% by weight. Correspondingly, OLEDs are currently produced in the prior art only with emitter molecule concentrations of about 2 to 8% by weight. However, the stacking observed in the case of the compounds employed in accordance with the invention at least partially overcomes the problems occurring in the prior art.

However, the use of high concentrations of emitter molecules in the emitter layer and in particular the provision of emitter layers having a crystalline or quasi-crystalline order gives a number of considerable advantages:

An emitter layer structure comprising uniform material results in a clearly defined and easily reproducible manufacturing situation.

Slight changes in the molecules employed allow different metal-metal separations to be set and thus interactions of different strength between the complexes. This results in the possibility of tuning the emission colour from blue to red and to the near IR. It is of particular importance that virtually any desired colour can be set through a slight chemical variation of the emitter molecules.

The emitter layers are simple to produce by vacuum sublimation processes (and if necessary subsequent slight heating).

The emitter monomer materials have good solubility in many solvents. These crystalline or quasi-crystalline emitter layers can thus also be produced by spin coating or ink-jet printing processes.

The emission quantum yields are very high.

The monomers also have good suitability for chemical linking to polymers. In the case of adjacent monomers, metal-metal interactions can again result, with the desired excellent emission properties.

The substances have extremely high chemical stability, which results in high OLED long-term stability.

Specific mixing of different materials (for example $Pd(CN)_2(CNR)_2$ with $Pt(CN)_2(CNR)_2$, at least one substance of which is described by the formula (I), allows further, independent variation of the properties.

Particular preference is given to the use of the emitters according to the invention having a columnar structure. This structure forms, in particular, in the case of high concentrations of the complexes in the emitter layer since, as indicated above, the complexes according to the invention themselves have a planar structure. Stacking one above the other and the formation of columnar structures is thus possible.

A further variation can be achieved through the formation of columnar structures from different complexes of the formula (I). All ligands and the central atom can be varied independently of one another here. Thus, for example, a first complex of the formula (I) having a first central atom M and a second complex of the formula (I) having a second central atom which is different from the first central atom are present in the emitter layer.

Further tuning of the emission wavelengths can be achieved by means of layers which comprise different complexes. The emitter layer preferably comprises at least one complex of the formula (I) where M=Pt and at least one complex of the formula (I) where M Pd. The weight ratio of the two complexes here is preferably 1:99 to 99:1. It is advantageous to provide an emitter layer in which a first complex is present predominantly and a second emitter complex only in suitable amounts, for example in the weight ratio 1:99 to 5:95.

The complexes employed in accordance with the invention as emitters, i.e. oligomers thereof, can be tuned in the wavelength range in a simple manner (through the choice of suitable matrix materials) and, in particular, through the choice of electron-withdrawing or electron-donating substituents.

Preference is given to the use of compounds which exhibit emission at a temperature of >−50° C., preferably >0° C., in particular at >10° C., and still more preferably at >20° C. and preferably at temperatures to above 100° C.

The compounds dicyanobis(isopropylisocyanide)platinum(II), $Pt(CN)_2(i-C_3H_7NC)_2$ dicyanobis(n-butylisocyanide)platinum(II), $Pt(CN)_2(n-C_4H_9NC)_2$ dicyanobis(cyclohexylisocyanide)platinum(II), $Pt(CN)_2(C_6H_{11}NC)_2$ dicyanobis((S)-(−)-α-methylbenzylisocyanide)platinum(II), $Pt(CN)_2(C_8H_9NC)_2$ dicyanobis(tert-butylisocyanide)palladium(II), $Pd(CN)_2(t-C_4H_9NC)_2$ and/or dicyanobis(isopropylisocyanide)palladium(II), $Pd(CN)_2(i-C_3H_7NC)_2$ and dicyanobis(methylisocyanide)platinum(II), $Pt(CN)_2(CH_3NC)_2$ dicyanobis(ethylisocyanide)platinum(II), Pt(CN)$_2$(C$_2$H$_5$NC)$_2$
dicyanobis(tert-butylisocyanide)platinum(II), Pt(CN)$_2$(t-C$_4$H$_9$NC)$_2$
dicyanobis(3-isocyanopropyltriethoxysilane)platinum(II), Pt(CN)$_2$—((OEt)$_3$SiC$_3$H$_6$NC)$_2$
dicyanobis(1,3-diisocyanopropane)platinum(II), Pt(CN)$_2$—(CNCH$_2$CH$_2$CH$_2$NC)$_2$
dicyanobis(2,5-dimethylphenylisocyanide)platinum(II), Pt(CN)$_2$(C$_8$H$_9$NC)$_2$
dicyanobis(3,3-difluorophenylisocyanide)platinum(II), Pt(CN)$_2$(C$_6$H$_3$F$_2$NC)$_2$
dicyanobis(3-isocyanomethylpyridine)platinum(II), Pt(CN)$_2$(C$_5$H$_4$NCH$_2$NC)$_2$
dicyanobis(2,2,2-trifluoroethylisocyanide)platinum(II), Pt(CN)$_2$—(CF$_3$CH$_2$CH$_2$NC)$_2$ are particularly preferably employed in accordance with the invention.

The invention furthermore relates to the use of a compound of the formula (I), as defined herein, as emitter in a light-emitting device, in particular in an organic light-emitting device.

The invention furthermore relates to isonitrile/palladium complexes of the formula (Ia) (NC)$_n$Pd(CNR)$_m$, where n, m and R are defined as indicated in this respect.

It has been found in accordance with the invention that oligomers or crystalline or quasi-crystalline layers of the complexes of the formula (I) described herein have high charge-carrier mobility. This property can be utilised in numerous applications, in particular in applications in which high charge-carrier mobility is advantageous or desired.

The materials described above herein and in particular the complexes of the formula (I) whose oligomers comprise crystalline or quasi-crystalline layers can also be used in solar cells. To this end, preference is given to the use of strongly absorbent materials of the formula (I). Solar cells function in accordance with a reversed OLED principle.

The invention furthermore relates to novel compounds which can be employed, in particular, for LED applications as described herein. The novel complexes are dicyanobis(isopropylisocyanide)platinum(II), Pt(CN)$_2$(i-C$_3$H$_7$NC)$_2$
dicyanobis(n-butylisocyanide)platinum(II), Pt(CN)$_2$(n-C$_4$H$_9$NC)$_2$
dicyanobis(cyclohexylisocyanide)platinum(II), Pt(CN)$_2$(C$_6$H$_{11}$NC)$_2$
dicyanobis((S)-(−)-α-methylbenzylisocyanide)platinum(II), Pt(CN)$_2$(C$_8$H$_9$NC)$_2$
dicyanobis(tert-butylisocyanide)palladium(II), Pd(CN)$_2$(t-C$_4$H$_9$NC)$_2$
dicyanobis(isopropylisocyanide)palladium(II), Pd(CN)$_2$(i-C$_3$H$_7$NC)$_2$
dicyanobis(isopropylisocyanide)palladium(II), Pd(CN)$_2$(i-C$_3$H$_7$NC)$_2$
dicyanobis(methylisocyanide)platinum(II), Pt(CN)$_2$(CH$_3$NC)$_2$
and
dicyanobis(2,5-dimethylphenylisocyanide)platinum(II), Pt(CN)$_2$(C$_8$H$_9$NC)$_2$
dicyanobis(1,3-diisocyanopropane)platinum(II), Pt(CN)$_2$(CNCH$_2$CH$_2$CH$_2$NC)
dicyanobis(3,4-difluorophenylisocyanide)platinum(II), Pt(CN)$_2$(C$_6$H$_3$F$_2$NC)$_2$
dicyanobis(3-isocyanomethylpyridine)platinum(II), Pt(CN)$_2$(C$_5$H$_4$NCH$_2$NC)$_2$
dicyanobis(2,2,2-trifluoroethylisocyanide)platinum(II), Pt(CN)$_2$(CF$_3$CH$_2$NC)$_2$
dicyanobis(methoxymethylisocyanide)platinum(II), Pt(CN)$_2$(CH$_3$OCH$_2$NC)$_2$
dicyanobis(4-fluorophenylisocyanide)platinum(II), Pt(CN)$_2$(C$_6$H$_4$FNC)$_2$
dicyanobis(4-methoxyphenylisocyanide)platinum(II), Pt(CN)$_2$(CH$_3$OC$_6$H$_4$NC)$_2$
dicyanobis(4-isocyanoacetophenone)platinum(II), Pt(CN)$_2$(CH$_3$COC$_6$H$_4$NC)$_2$
dicyanobis(2-naphthylisocyanide)platinum(II), Pt(CN)$_2$(C$_{10}$H$_7$NC)$_2$
dicyanobis(4-chlorophenylisocyanide)platinum(II), Pt(CN)$_2$(C$_6$H$_4$ClNC)$_2$
dicyanobis(4-bromophenylisocyanide)platinum(II), Pt(CN)$_2$(C$_6$H$_4$ClNC)$_2$
dicyanobis(4-nitrophenylisocyanide)platinum(II), Pt(CN)$_2$(O$_2$NC$_6$H$_4$NC)$_2$
dicyanobis(methyl-3-isocyano-4-methylbenzoate)platinum(II), Pt(CN)$_2$(C$_9$H$_9$O$_2$NC)$_2$
dicyanobis(4-isocyanobenzotrifluoride)platinum(II), Pt(CN)$_2$(CF$_3$C$_6$H$_4$NC)$_2$
dicyanobis(4-(methylthio)phenylisocyanide)platinum(II), Pt(CN)$_2$(CH$_3$SC$_6$H$_4$NC)$_2$
dicyanobis(4-methylphenylisocyanide)platinum(II), Pt(CN)$_2$(CH$_3$C$_6$H$_4$NC)$_2$
dicyanobis(4-tert-butylphenylisocyanide)platinum(II), Pt(CN)$_2$((CH$_3$)$_3$CC$_6$H$_4$NC)$_2$
dicyanobis(3,4,5-trimethoxyphenylisocyanide)platinum(II), Pt(CN)$_2$(C$_9$H$_{11}$O$_3$NC)$_2$
dicyanobis(4-formylaminophenylisocyanide)platinum(II), Pt(CN)$_2$(C$_7$H$_6$NONC)$_2$
dicyanobis(4-butoxyphenylisocyanide)platinum(II), Pt(CN)$_2$(C$_4$H$_9$OC$_6$H$_4$NC)$_2$
dicyanobis(4-(trifluoromethoxy)phenylisocyanide)platinum(II), Pt(CN)$_2$(CF$_3$OC$_6$H$_4$NC)$_2$
dicyanobis(4-vinylphenylisocyanide)platinum(II), Pt(CN)$_2$(C$_8$H$_7$NC)$_2$
dicyanobis(1-cyclohexenylisocyanide)platinum(II), Pt(CN)$_2$(C$_6$H$_9$NC)$_2$
dicyanobis(2-(thien-2-yl)ethylisocyanide)platinum(II), Pt(CN)$_2$(C$_6$H$_7$SNC)$_2$
dicyanobis(5-methylfurfurylisocyanide)platinum(II), Pt(CN)$_2$(C$_6$H$_7$ONC)$_2$
dicyanobis(N-(2-isocyanoethyl)imidazole)platinum(II), Pt(CN)$_2$(C$_5$H$_7$N$_2$NC)$_2$
dicyanobis(6-isocyanoquinolino)imidazole)platinum(II), Pt(CN)$_2$(C$_9$H$_6$NNC)$_2$
dicyanobis(4-isocyanomethylpyridine)platinum(II), Pt(CN)$_2$(C$_5$H$_4$NCH$_2$NC)$_2$
dicyanobis(allylisocyanide)platinum(II), Pt(CN)$_2$(C$_3$H$_5$NC)$_2$
dicyanobis(2-isocyanoethyltosylate)platinum(II), Pt(CN)$_2$(C$_9$H$_{11}$O$_3$SNC)$_2$
dicyanobis(propylisocyanide)platinum(II), Pt(CN)$_2$(C$_3$H$_7$NC)$_2$
dicyanobis(2-(morpholino)cyanoethane)platinum(II), Pt(CN)$_2$(CNCH$_2$C$_4$H$_8$NO)$_2$
dicyanobis(2-(thiazolidino)cyanoethane)platinum(II), Pt(CN)$_2$(CNCH$_2$C$_3$H$_6$S)$_2$
dicyanobis(2-(methylpiperazino)cyanoethane)platinum(II), Pt(CN)$_2$(CNCH$_2$C$_5$H$_{11}$N$_2$)$_2$
dicyanobis(2-(ethylenedioxypiperazino)cyanoethane)platinum(II), Pt(CN)$_2$(CNCH$_2$C$_6$H$_{12}$N$_2$O$_2$)$_2$
dicyanobis(1-isocyanoindane)platinum(II), Pt(CN)$_2$(CNC$_9$H$_9$)$_2$
dicyanobis(4-methoxybenzylisocyanide)platinum(II), Pt(CN)$_2$(CNCH$_2$C$_6$H$_4$OCH$_3$)$_2$ dicyanobis(1-isocyano-1,2,3,4-tetrahydronaphthalene)platinum(II), $Pt(CN)_2(CNC_{10}H_{11})_2$
dicyanobis(5-isocyanomethylbenzo[4,5]-1,3-dioxolane) platinum(II), $Pt(CN)_2(CNCH_2C_7H_5O_2)_2$
dicyanobis(4-tert-butylbenzylisocyanide)platinum(II), $Pt(CN)_2(CNCH_2C_{10}H_{13})_2$
dicyanobis(3,5-dimethylbenzylisocyanide)platinum(II), $Pt(CN)_2(CNCH_2C_8H_9)_2$
dicyanobis(3-methoxybenzylisocyanide)platinum(II), $Pt(CN)_2(CNCH_2C_7H_7O)_2$
dicyanobis(1-(4-fluorophenyl)methylisocyanide)platinum(II), $Pt(CN)_2(CNCH_2C_6H_4F)_2$
dicyanobis(4-(trifluoromethoxy)benzylisocyanide)platinum(II), $Pt(CN)_2(CNCH_2C_7H_4F_3O)_2$
dicyanobis(2,6-difluorobenzylisocyanide)platinum(II), $Pt(CN)_2(CNCH_2C_6H_3F_2)_2$
dicyanobis(2-(trifluoromethyl)benzylisocyanide)platinum(II), $Pt(CN)_2(CNCH_2C_7H_4F_3)_2$
dicyanobis(4-(trifluoromethypenzylisocyanide)platinum(II), $Pt(CN)_2(CNCH_2C_7H_4F_3)_2$
dicyanobis(3,4,5-trimethoxybenzylisocyanide)platinum(II), $Pt(CN)_2(CNCH_2C_9H_{11}O_3)_3$
dicyanobis(triphenylisocyanomethane)platinum(II), $Pt(CN)_2(CNC_{19}H_{15})_2$
dicyanobis(2,6-dichlorobenzylisocyanide)platinum(II), $Pt(CN)_2(CNCH_2C_6H_3Cl_3)_2$
dicyanobis(2,3-dimethylbenzylisocyanide)platinum(II), $Pt(CN)_2(CNCH_2C_8H_9)_2$
dicyanobis(4-trifluoromethylbenzylisocyanide)platinum(II), $Pt(CN)_2(CNCH_2C_6H_4CF_3)_2$
dicyanobis(cycloheptylisocyanide)platinum(II), $Pt(CN)_2(CNC_7H_{14})_2$
dicyanobis(isocyanooctane)platinum(II), $Pt(CN)_2(CNC_8H_{17})_2$
dicyanobis(1-isocyano-3-isopropoxypropane)platinum(II), $Pt(CN)_2(CNC_6H_{13}O)_2$
dicyanobis(3,3-dimethylbut-1-ylisocyanide)platinum(II), $Pt(CN)_2(CNC_6H_{13}O)_2$ Further preferred compounds according to the invention are the analogous Pd complexes.

The invention is explained further by the attached figures and the following examples.

BRIEF DESCRIPTION OF THE DRAWINGS

FIG. 1 shows an example of an OLED device manufactured by means of vacuum sublimation. Good efficiency is achieved, even with a 100% layer of the complexes according to the invention, without the use of a UGH matrix material.

FIG. 3 shows an example of an OLED device comprising emitters according to the invention, which are applied by wet-chemical methods. The layer-thickness data should be regarded as illustrative values.

EXAMPLES

Example 1

The complexes according to the invention can be prepared by heating the double-complex salt (Eq. 1) or dissolving the salt in $CHCl_3$ or by alkylation of the

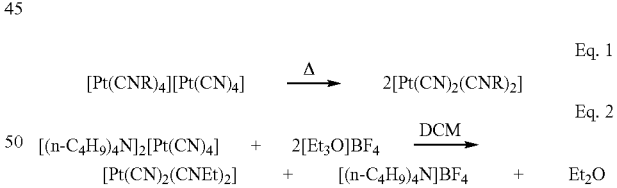

A special synthesis is possible for R=$^t$Bu (Eq. 3):

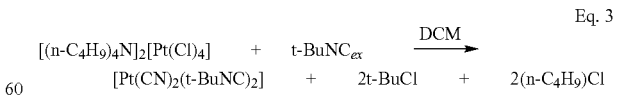

H. Isci, W. R. Mason, Inorg. Chem. 1975, 14, 913.

Analogously to the synthesis of (bisphosphine)Pt(CN)$_2$ complexes, new synthetic access starting from sparingly soluble Pt(CN)$_2$ and the corresponding isonitrile was selected (Eq. 4):

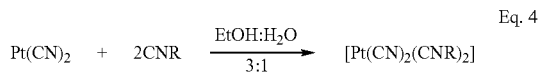

Eq. 4

2 V. Pawlowski, H. Kunkely, C. Lennartz, K. Bohn, A. Vogler, *Eur. J. Inorg. Chem.* 2004, 4242.

R=alkyl, aryl, heteroaryl, —$SO_2R'$, and functionalised derivatives, and polydentate derivatives (for example $CNCH_2CH_2CH_2NC$).

The isonitriles can be obtained by elimination of water from monosubstituted formamides.

3 I. Ugi, U. Fetzer, U. Eholzer, H. Knupfer, K. Offermann, *Anger. Chem.* 1965, 77, 492.

The neutral palladium complexes [$Pd(CN)_2(CNR)_2$] are prepared analogously to the Pt complexes from $Pd(CN)_2$ and the corresponding isonitrile RNC.

Example 2

2.1. Preparation of dicyanobis(tert-butylisocyanide) platinum(II), $Pt(CN)_2(t-C_4H_9NC)_2$ tert-Butyl isocyanide (0.184 ml, 0.135 g, 1.62 mmol) in an ethanol/water mixture (8 ml, volume ratio ethanol/water 3:1) is added to a suspension of $Pt(CN)_2$ (0.200 g, 0.81 mmol) in an ethanol/water mixture (40 ml, volume ratio ethanol/water 3:1). The suspension is stirred at room temperature for three days. The resultant yellow-green solution is filtered to remove unconsumed $Pt(CN)_2$, and the solvent mixture is removed in vacuo. The green solid remaining is taken up in a little acetonitrile, and the product is precipitated using ether. The precipitated green solid is filtered off and dried in a desiccator. Crystals which are suitable for X-ray structural analysis are obtained from acetonitrile/ether. The sample exhibits strong green luminescence on irradiation with ultraviolet light, for example having a wavelength of 365 nm.

Figure 2:
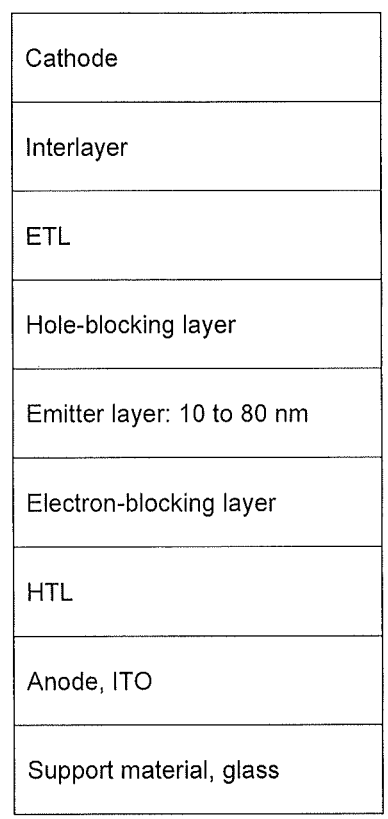
FIG. 2 shows an example of a differentiated highly efficient OLED device comprising sublimable emitter materials according to the invention.
Figure 4:
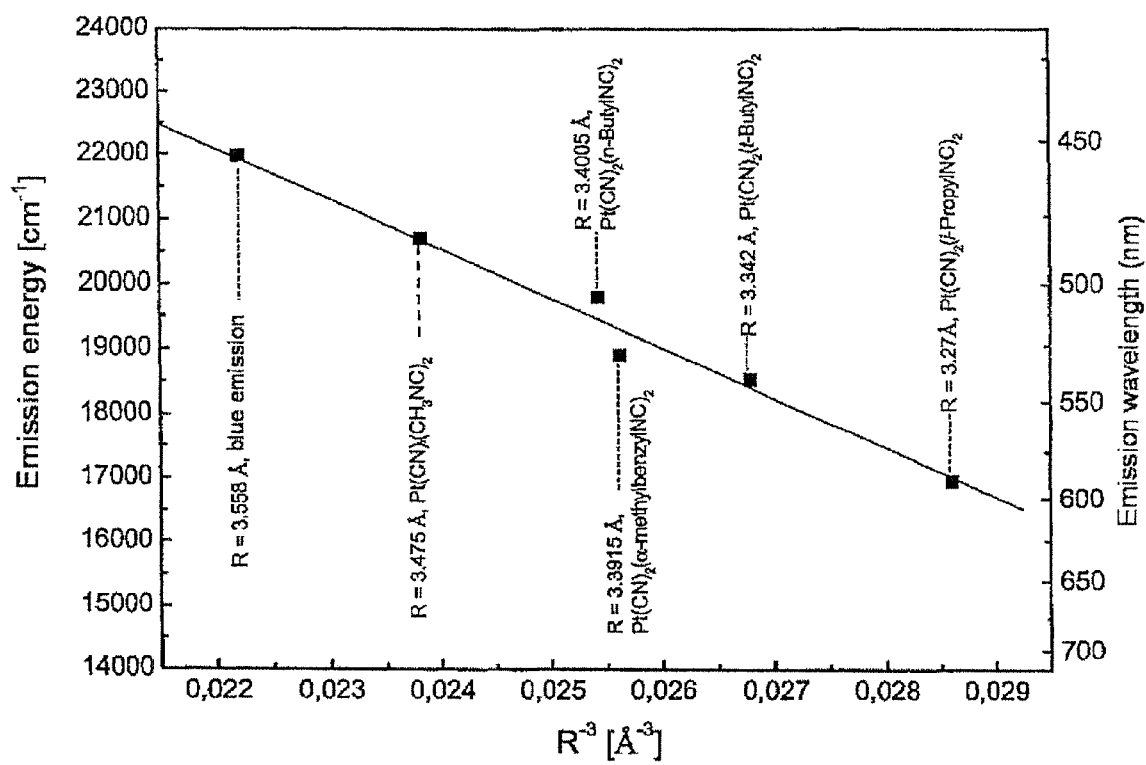
FIG. 4 shows the room-temperature emission maxima against $R^{-3}$ for $Pt(CN)_2(RNC)_2$ compounds. R is the Pt—Pt separation in the complex stacks. In the case of compounds having two different Pt—Pt separations in the chain, the R average was used for the plot.
Figure 5:
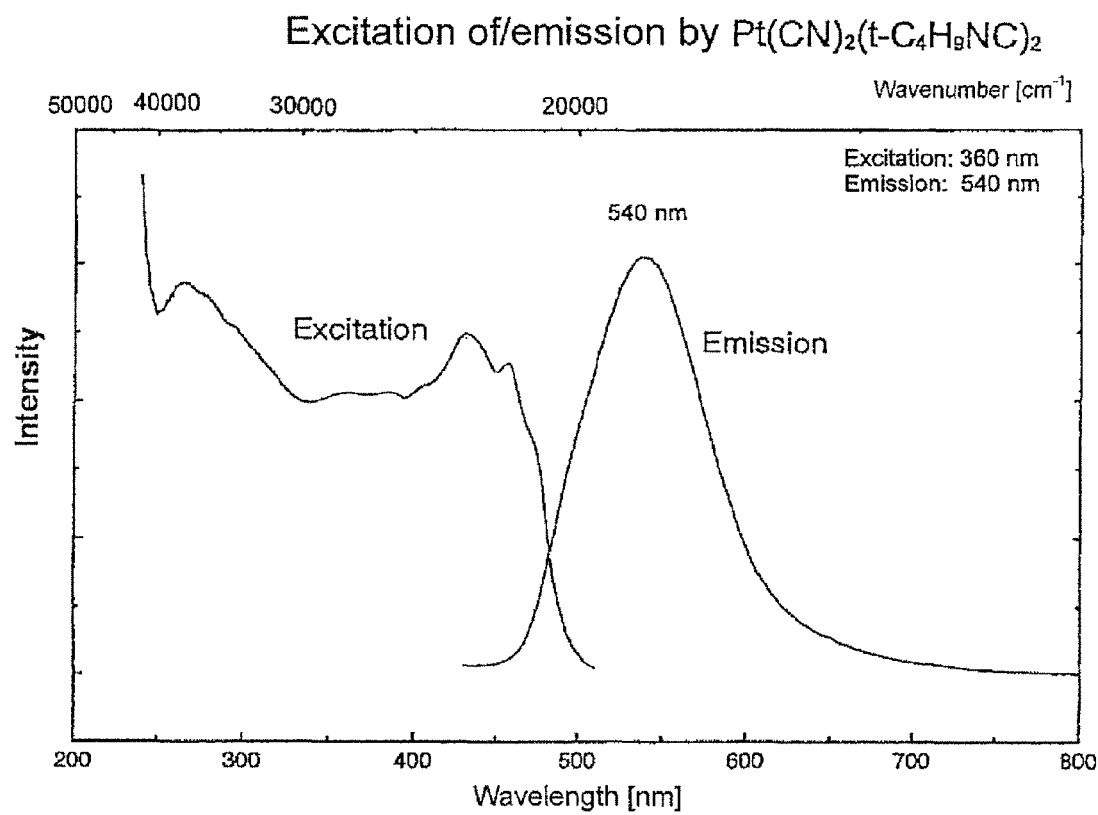
FIG. 5 shows the emission and excitation spectrum of $Pt(CN)_2(t-C_4H_9NC)_2$. $\lambda_{exc}$=360 nm, $\lambda_{det}$=540 nm, relaxation time τ=1.2 μs, T=300 K.
Figure 6:
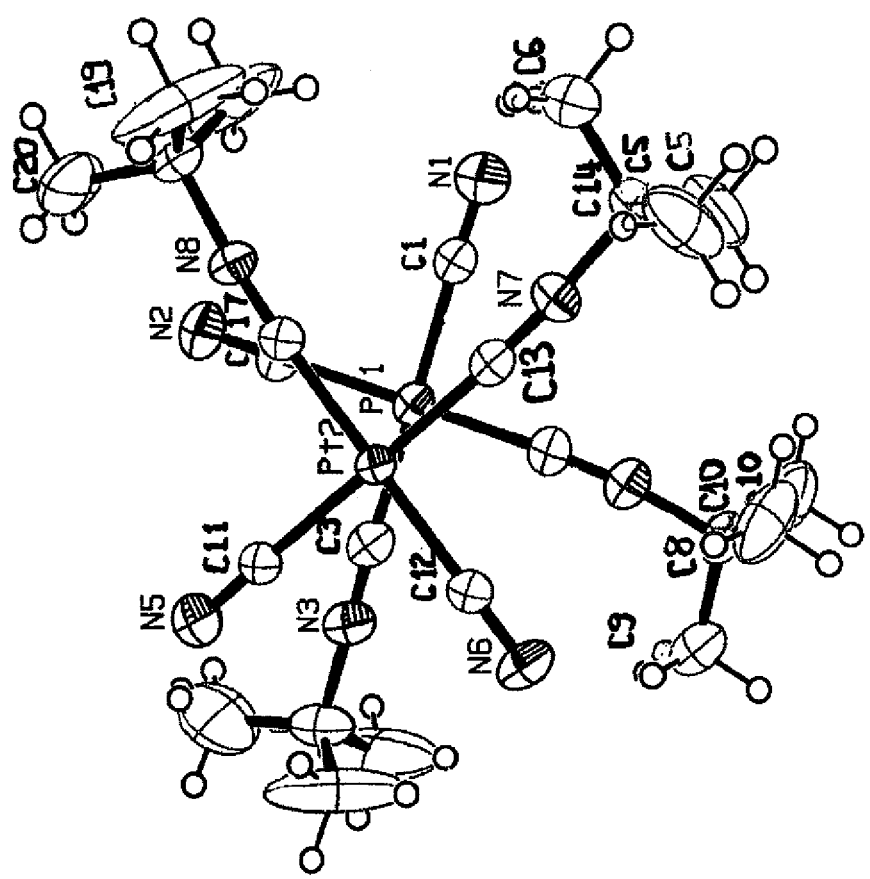
FIG. 6 shows the X-ray structure of dicyanobis(tert-butylisocyanide)-platinum(II). Pt—Pt separation R=3.342 Å.

Empirical formula: $C_{12}H_{18}N_4Pt$ (413.38 g/mol)
Yield: 0.266 g (79%)
Mass spectrometry: ES-MS, m/e=414.1 M+H$^+$, 100%
(see in this respect FIGS. 5 and 6)

2.2. Preparation of dicyanobis(isopropylisocyanide) platinum(II), $Pt(CN)_2(i-C_3H_7NC)_2$ Isopropyl isocyanide (0.39 ml, 0.286 g, 4.14 mmol) in an ethanol/water mixture (8 ml, volume ratio ethanol/water 3:1) is added to a suspension of $Pt(CN)_2$ (0.512 g, 2.07 mmol) in an ethanol/water mixture (40 ml, volume ratio ethanol/water 3:1). The suspension is stirred at room temperature for seven days. The resultant cloudy yellow solution is filtered to remove unconsumed $Pt(CN)_2$, and the solvent mixture is removed in vacuo. The yellow-orange solid remaining is taken up in a little acetonitrile. The solution is filtered to remove undissolved impurities remaining, and the product is precipitated using ether. The precipitated orange solid is filtered off and dried in a desiccator. Crystals which are suitable for X-ray structural analysis are obtained from acetonitrile/ether. The sample exhibits strong yellow-orange luminescence on irradiation with ultraviolet light, for example having a wavelength of 365 nm.

Figure 7:
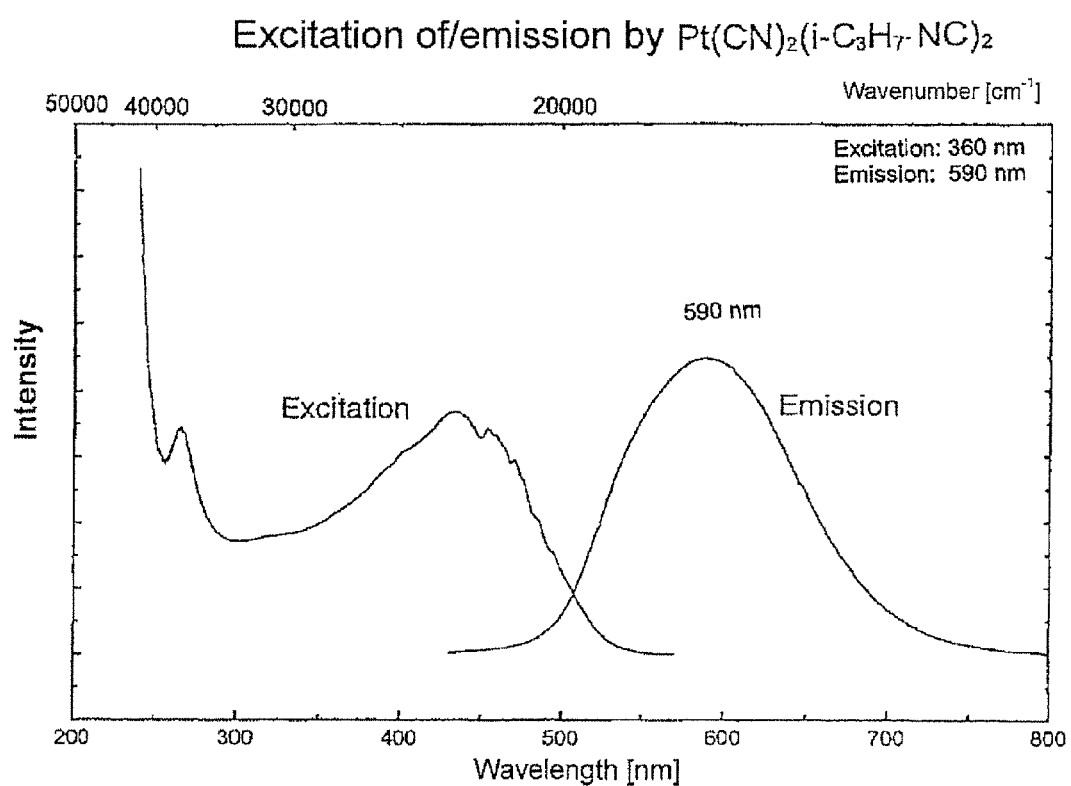
FIG. 7 shows the emission and excitation spectrum of $Pt(CN)_2(i-C_3H_7-NC)_2$. $\lambda_{exc}$=360 nm, $\lambda_{det}$=590 nm, relaxation time τ=1.6 μs, T=300 K.
Figure 8:
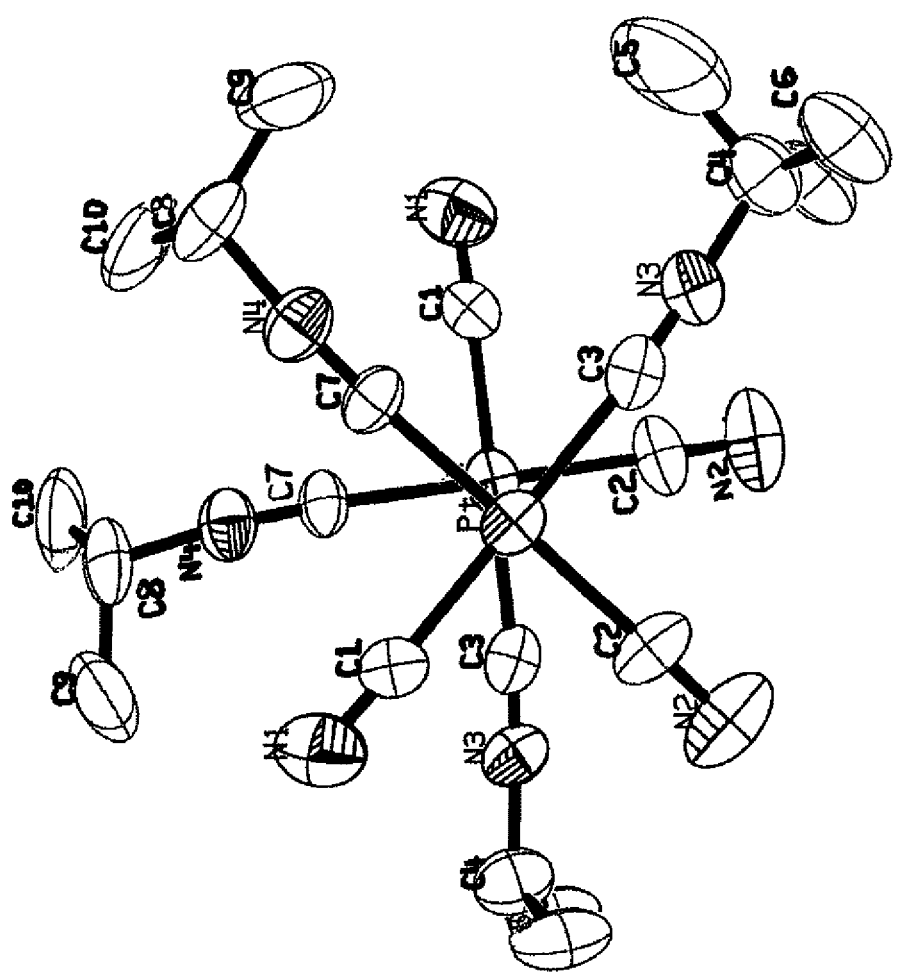
FIG. 8 shows the X-ray structure of dicyanobis(isopropylisocyanide)platinum(II). Pt—Pt separation R=3.270 Å.

Empirical formula: $C_{10}H_{14}N_4Pt$ (385.32 g/mol)
Yield: 0.523 g (66%)
Elemental analysis: $C_{10}H_{14}N_4Pt$ (385.32 g/mol) calculated: C, 31.17; H, 3.66; N, 14.54. found: C, 30.58; H, 4.40; N, 14.50.
Mass spectrometry: ES-MS, m/e=386.1 M+H$^+$, 100%
(see in this respect FIGS. 7 and 8)

2.3. Preparation of dicyanobis(n-butylisocyanide) platinum(II), $Pt(CN)_2(n-C_4H_9NC)_2$ n-Butyl isocyanide (0.36 ml, 0.283 g, 3.40 mmol) in an ethanol/water mixture (8 ml, volume ratio ethanol/water 3:1) is added to a suspension of $Pt(CN)_2$ (0.420 g, 1.7 mmol) in an ethanol/water mixture (40 ml, volume ratio ethanol/water 3:1). The suspension is stirred at room temperature for seven days. The resultant cloudy pale-green solution is filtered to remove unconsumed $Pt(CN)_2$, and the solvent mixture is removed in vacuo. The green-yellow solid remaining is taken up in a little acetonitrile. The solution is filtered to remove undissolved impurities remaining, and the product is precipitated using ether. The precipitated green-yellow solid is filtered off and dried in a desiccator. Crystals which are suitable for X-ray structural analysis are obtained from acetonitrile/ether. The sample exhibits strong blue-green luminescence on irradiation with ultraviolet light, for example having a wavelength of 365 nm.

Figure 9:
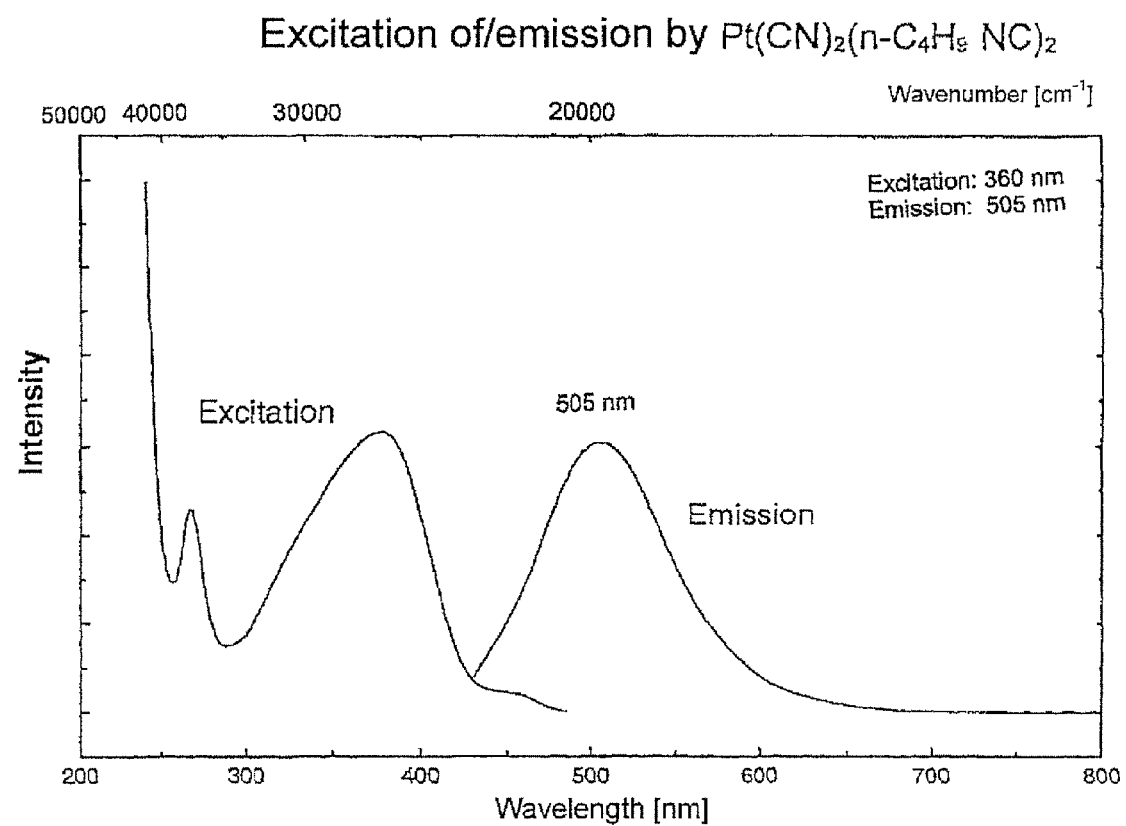
FIG. 9 shows the emission and excitation spectrum of $Pt(CN)_2(n-C_4H_9NC)_2$. $\lambda_{exc}$=360 nm, $\lambda_{det}$=505 nm, relaxation time τ=1.2 μs, T=300 K.
Figure 10:
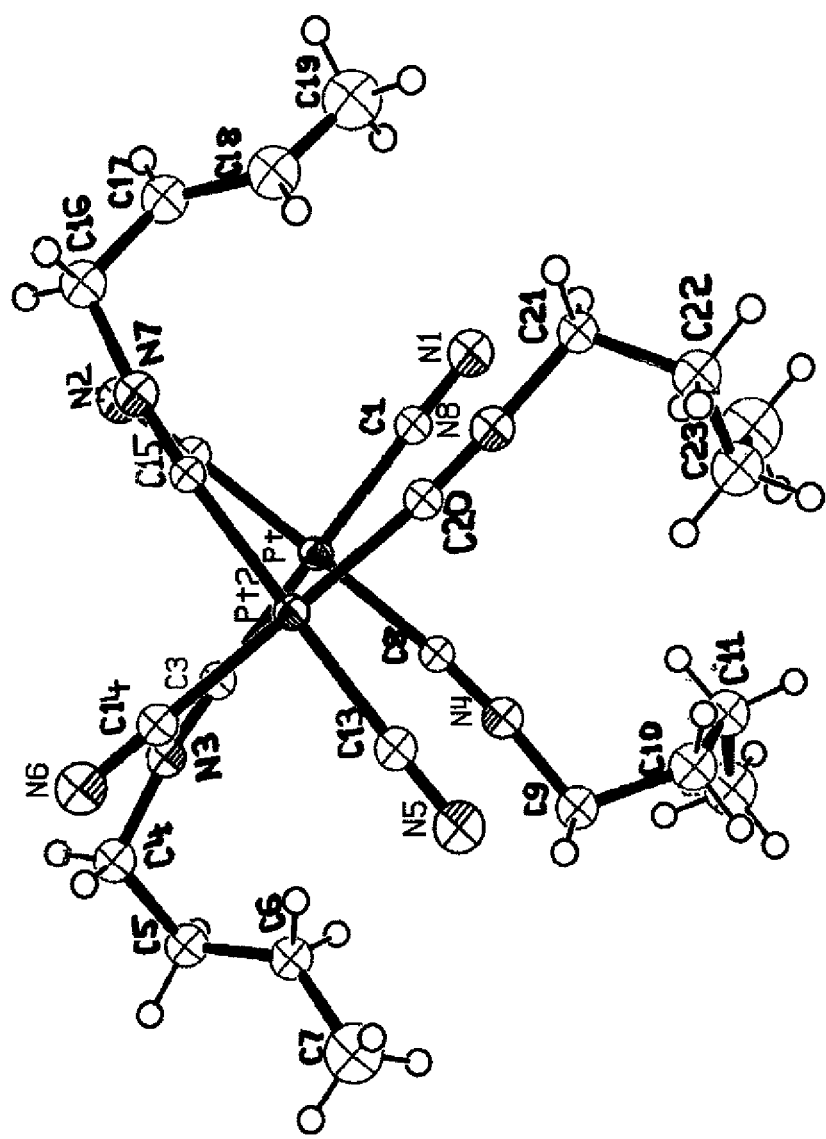
FIG. 10 shows the X-ray structure of dicyanobis(n-butylisocyanide)platinum(II). Pt—Pt separations $R_1$=3.387 Å, $R_2$=3.414 Å.

Empirical formula: $C_{12}H_{18}N_4Pt$ (413.38 g/mol)
Elemental analysis: $C_{12}H_{18}N_4Pt$ (413.38 g/mol) calculated: C, 34.87; H, 4.39; N, 13.55. found: C, 34.30; H, 4.21; N, 13.75.
Mass spectrometry: ES-MS, m/e=414.1 M+H$^+$, 100%
(see in this respect FIGS. 9 and 10)

2.4. Preparation of dicyanobis(cyclohexylisocyanide) platinum(II), $Pt(CN)_2(C_6H_{11}NC)_2$ Cyclohexyl isocyanide (0.40 ml, 0.356 g, 3.26 mmol) in an ethanol/water mixture (8 ml, volume ratio ethanol/water 3:1) is added to a suspension of $Pt(CN)_2$ (0.402 g, 1.63 mmol) in an ethanol/water mixture (40 ml, volume ratio ethanol/water 3:1). The suspension is stirred at room temperature for seven days. The resultant cloudy pale-yellow solution is filtered to remove unconsumed $Pt(CN)_2$, and the solvent mixture is removed in vacuo. The yellow solid remaining is taken up in a little acetonitrile. The solution is filtered to remove undissolved impurities remaining, and the product is precipitated using ether. The precipitated yellow solid is filtered off and dried in a desiccator. The sample exhibits strong yellow luminescence on irradiation with ultraviolet light, for example having a wavelength of 365 nm.

Figure 11:
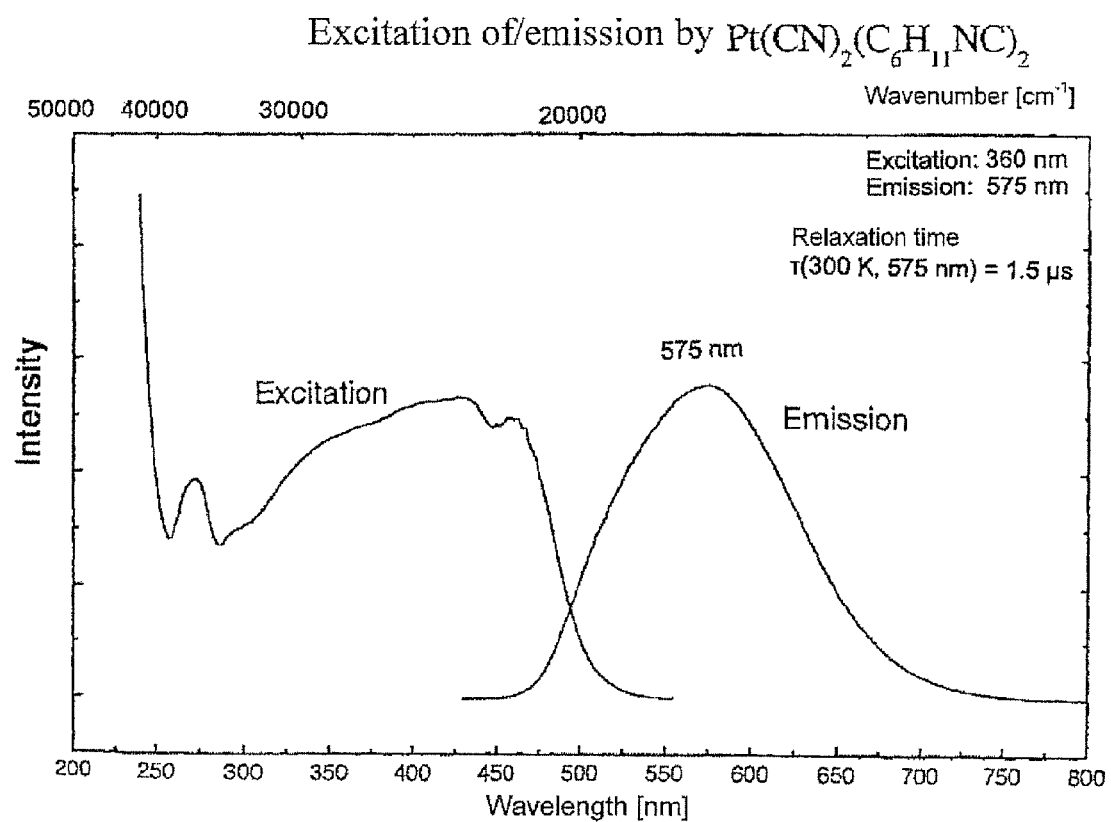
FIG. 11 shows the emission and excitation spectrum of $Pt(CN)_2(C_6H_{11}NC)_2$. $\lambda_{exc}$=360 nm, $\lambda_{det}$=575 nm, relaxation time τ=1.5 μs, T=300K.

Empirical formula: $C_{16}H_{22}N_4Pt$ (465.45 g/mol)
Elemental analysis: $C_{16}H_{22}N_4Pt$ (465.45 g/mol) calculated: C, 41.29; H, 4.76; N, 12.04. found: C, 40.83; H, 5.01; N, 12.16.
Mass spectrometry: ES-MS, m/e=466.2 M+H$^+$, 100%
(see in this respect FIG. 11)

2.5. Preparation of dicyanobis(ethylisocyanide)platinum(II), $Pt(CN)_2(C_2H_5NC)_2$ $Pt(CN)_2(C_2H_5NC)_2$ is prepared by reaction of $(n-Bu_4N)_2[Pt(CN)_4]$ (1.180 g, 1.5 mmol) with $(C_2H_5)_3OBF_4$ (0.570 g, 3.00 mmol) in accordance with the method of H. Isci and W. R. Mason. The starting compound $(n-Bu_4N)_2$—$[Pt(CN)_4]$ required for this purpose is prepared in accordance with the method of W. R. Mason III and H. B. Gray.

4 H. Isci, W. R. Mason, *Inorg. Chem.* 1975, 14, 913.
5 W. R. Mason III, H. B. Gray, *J. Am. Chem. Soc.* 1968, 90, 5721.

Empirical formula: $C_8H_{10}N_4Pt.H_2O$ (375.29 g/mol)

Elemental analysis: $C_8H_{10}N_4Pt \cdot H_2O$ (375.29 g/mol) calculated: C, 25.60; H, 3.22; N, 14.93. found: C, 25.78; H, 3.14; N, 14.99.

Figure 12:
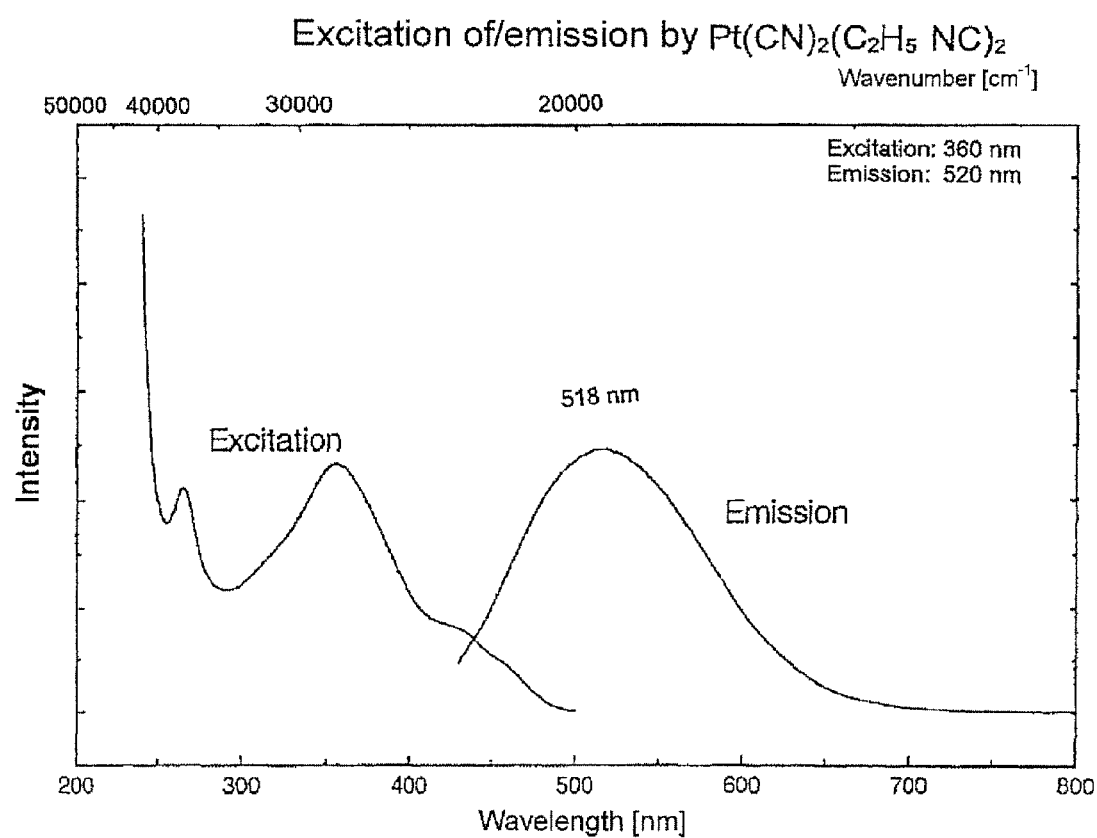
FIG. 12 shows the emission and excitation spectrum of $Pt(CN)_2(C_2H_5NC)_2$. $\lambda_{exc}$=360 nm, $\lambda_{det}$=520 nm, relaxation time τ=1.3 μs, T=300 K.

The X-ray structure can be obtained from ref.
(see in this respect FIG. 12)

6 P. J. Martellaro, S. K. Hurst, R. Larson, E. H. Abbott, E. S. Peterson, *Inorg. Chim. Acta.* 2005, 358, 3377.

2.6. Preparation of dicyanobis(methylisocyanide)platinum(II), $Pt(CN)_2(CH_3NC)_2$ Methyl isocyanide (0.168 g, 4.1 mmol) in an ethanol/water mixture (8 ml, volume ratio ethanol/water 3:1) is added to a suspension of $Pt(CN)_2$ (0.506 g, 2.05 mmol) in an ethanol/water mixture (40 ml, volume ratio ethanol/water 3:1). The suspension is stirred at room temperature for four days. The resultant cloudy pale-yellow solution is filtered to remove unconsumed $Pt(CN)_2$, and the solvent mixture is removed in vacuo. The yellow-green solid remaining is dried in a desiccator. The sample exhibits strong sky-blue luminescence on irradiation with ultraviolet light, for example having a wavelength of 365 nm.

Empirical formula: $C_6H_6N_4Pt$ (329.22 g/mol)
Elemental analysis: $C_6H_6N_4Pt$ (329.22 g/mol) calculated: C, 21.89; H, 1.84; N, 17.02. found: C, 21.49; H, 2.44; N, 17.48.
Mass spectrometry: ES-MS, m/e=330 M+H$^+$, 100%

Figure 13:
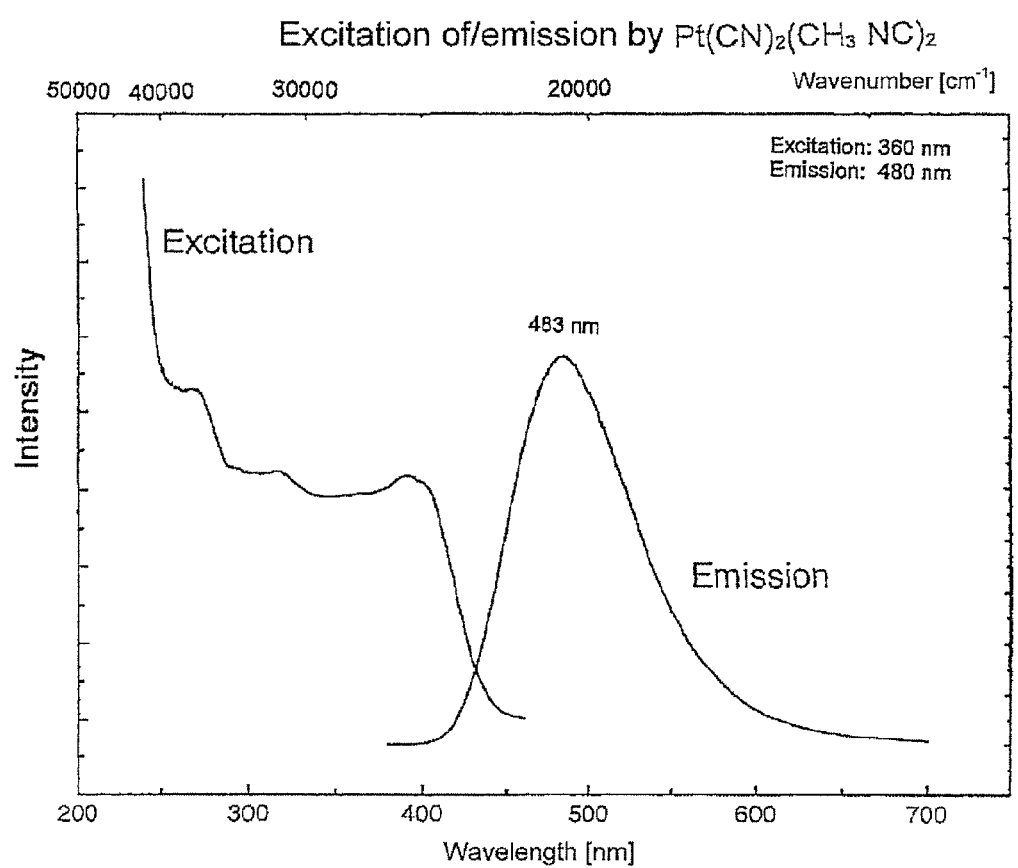
FIG. 13 shows the emission and excitation spectrum of $Pt(CN)_2(CH_3NC)_2$. $\lambda_{exc}$=360 nm, $\lambda_{det}$=480 nm, relaxation time τ=1.5 μs, T=300 K.

The X-ray structure can be obtained from ref.
(see in this respect FIG. 13)

6 P. J. Martellaro, S. K. Hurst, R. Larson, E. H. Abbott, E. S. Peterson, *Inorg. Chim. Acta.* 2005, 358, 3377.

2.7. Preparation of dicyanobis(tert-butylisocyanide) palladium(II), $Pd(CN)_2(t-C_4H_9NC)_2$ tert-Butyl isocyanide (0.34 g, 4.0 mmol) is added dropwise to a suspension of $Pd(CN)_2$ (0.320 g, 2.0 mmol) in 25 ml of DMF, and the mixture is stirred at room temperature for 24 hours. 100 ml of diethyl ether are added to the resultant clear solution with white solid, and the mixture is cooled to −30° C. The precipitated solid is filtered off with suction, washed with diethyl ether and dried over silica gel.

Empirical formula: $C_{12}H_{18}N_4Pd$ (324.72 g/mol)
Yield: 0.350 g (54%)
Elemental analysis: $C_{12}H_{18}N_4Pd$ (324.72 g/mol) calculated: C, 44.39; H, 5.59; N, 17.25. found: C, 44.23; H, 5.64; N, 17.49.
Mass spectrometry: ES-MS, m/e=325 M+H$^+$, 100%

2.8. Preparation of dicyanobis(isopropylisocyanide) palladium(II), $Pd(CN)_2(i-C_3H_7NC)_2$ The reaction is carried out under argon.

Isopropyl isocyanide (0.440 g, 6.3 mmol) is added dropwise to a suspension of $Pd(CN)_2$ (0.480 g, 3.0 mmol) in 25 ml of DMF, and the mixture is stirred at room temperature for 20 hours. During this time, the $Pd(CN)_2$ dissolves completely, and a clear pale-yellow solution is obtained. The solution is cooled in an ice bath, and 200 ml of diethyl ether are added. The precipitated white solid is filtered off, washed with diethyl ether and dried over silica gel.

Figure 14:
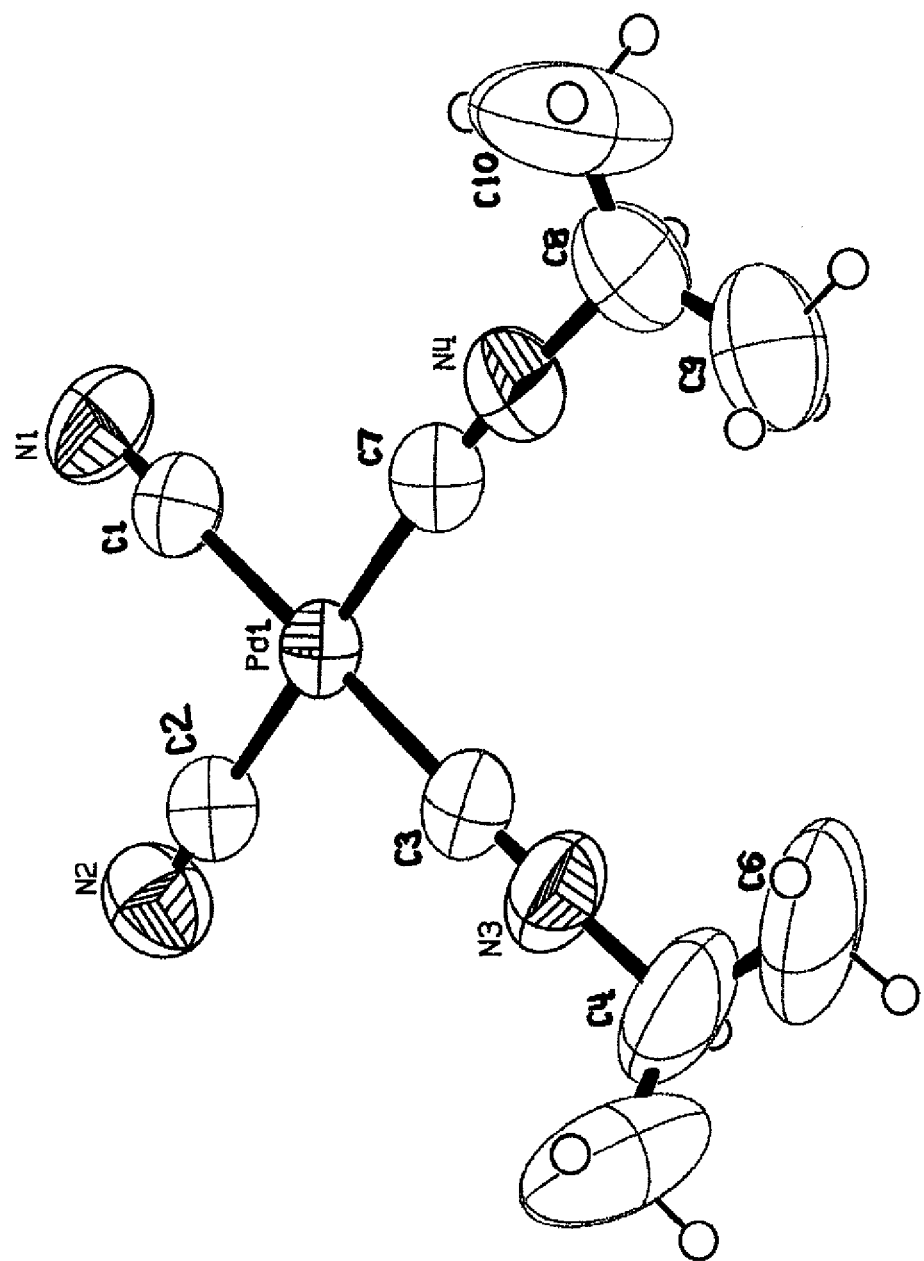
FIG. 14 shows the X-ray structure of dicyanobis(isopropylisocyanide)palladium(II). Pd—Pd separations $R_1$=3.473 Å, $R_2$=3.857 Å.

Empirical formula: $C_{10}H_{14}N_4Pd$ (296.67 g/mol)
Yield: 0.560 g (63%)
Elemental analysis: $C_{10}H_{14}N_4Pd$ (296.67 g/mol) calculated: C, 40.49; H, 4.76; N, 18.89. found: C, 40.39; H, 4.74; N, 19.60.
(see in this respect FIG. 14)

2.9. Blue- or White-Emitting Layers

A small amount of doping of $Pt(CN)_2(CNR)_2$ complexes in $Pd(CN)_2(CNR')_2$, where R=R' or R≠R', enables the emission range of the OLED to be shifted over broad ranges. Thus, blue, but also white emission can be produced.

2.9.1. Description of an Example

Figure 15:
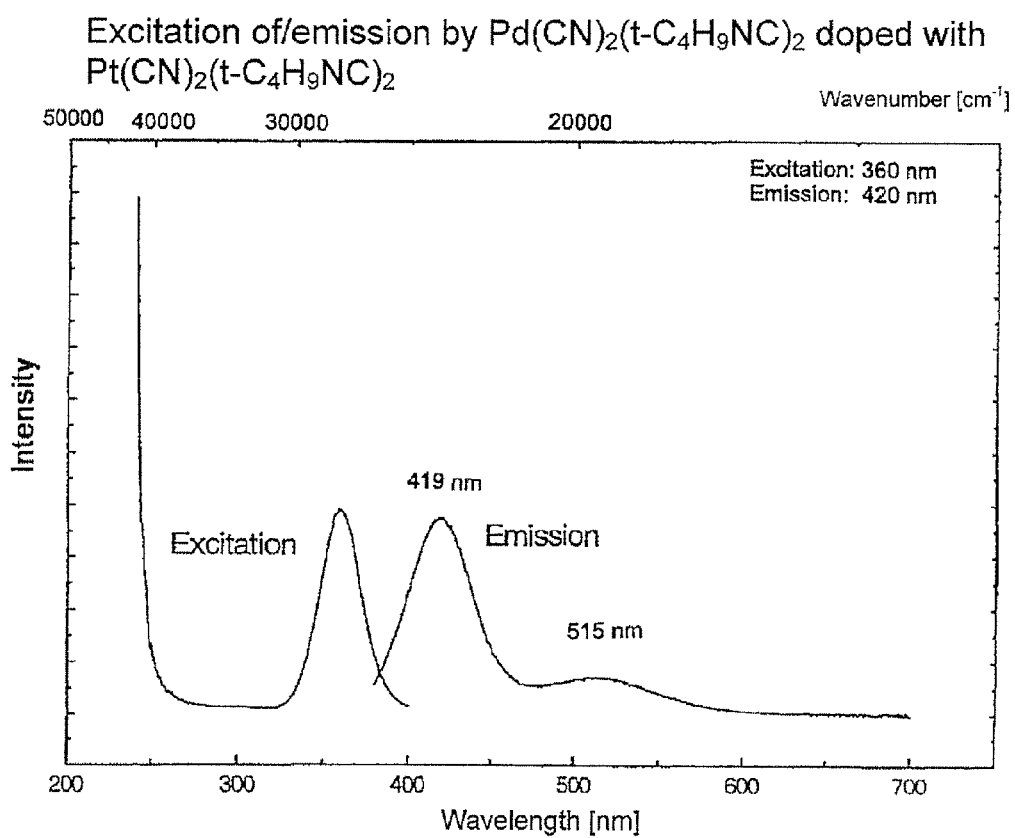
FIG. 15 shows the emission and excitation spectrum of $Pd(CN)_2(t-C_4H_9NC)_2$ doped with a small percentage of $Pt(CN)_2(t-C_4H_9NC)_2$. $\lambda_{exc}$=60 nm, $\lambda_{det}$=420 nm, T=300K.
Figure 16:
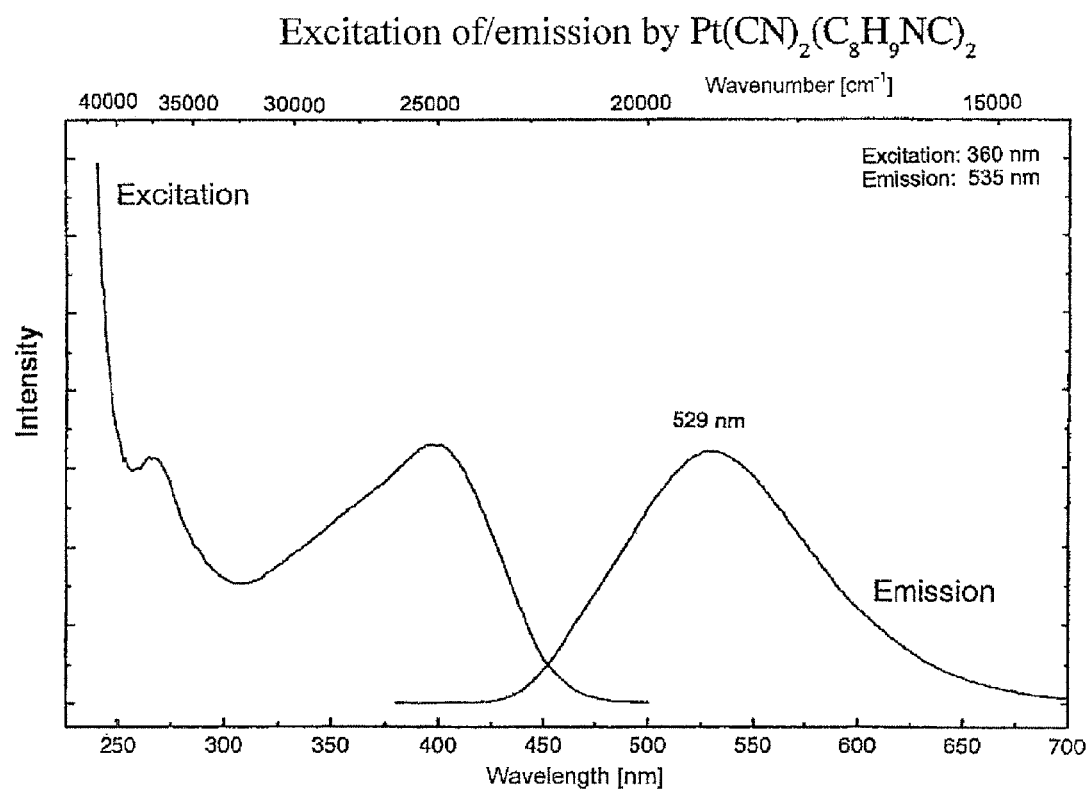
FIG. 16 shows the emission and excitation spectrum of $Pt(CN)_2(C_8H_9NC)_2$ (dicyanobis((S)-(−)-α-methylbenzylisocyanide)platinum(II). The Pt—Pt separations in the X-ray structure are $R_1$=3.325 Å, $R_2$=3.458 Å.
Figure 17:
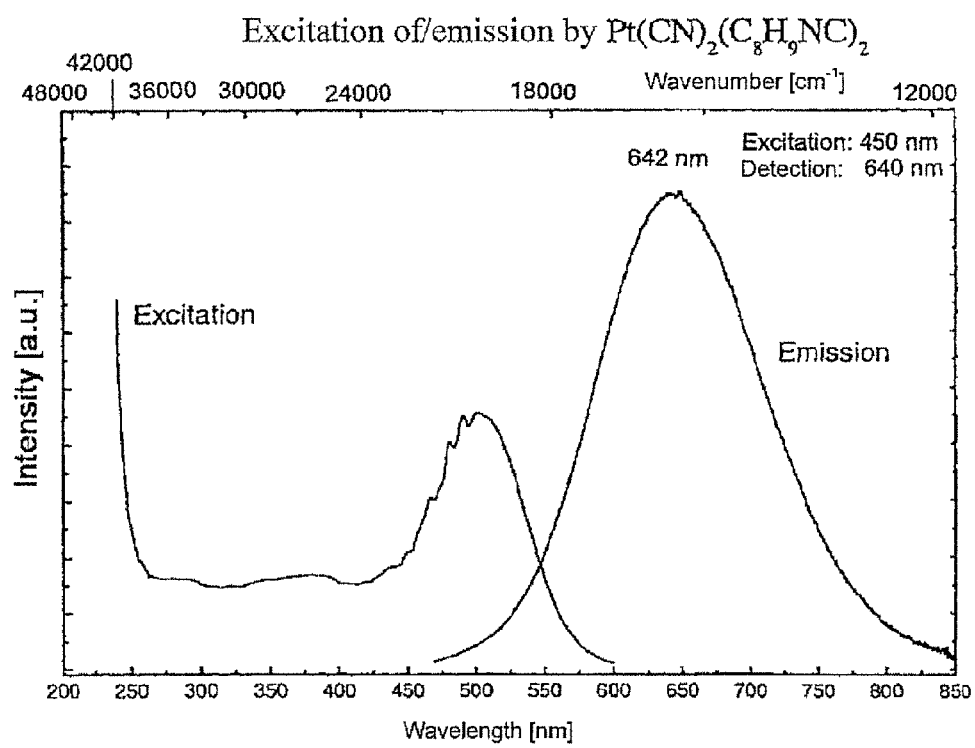
FIG. 17 shows the emission and excitation spectrum of $Pt(CN)_2(C_8H_9NC)_2$ (dicyanobis(2,5-dimethylphenylisocyanide)platinum(II)).

Doping of dicyanobis(tert-butylisocyanide)palladium(II), $Pd(CN)_2(t-C_4H_9NC)_2$, with dicyanobis(tert-butylisocyanide)platinum(II), $Pt(CN)_2(t-C_4H_9NC)_2$ A solution of each of $Pt(CN)_2(t-C_4H_9NC)_2$ and $Pd(CN)_2(t-C_4H_9NC)_2$ in dichloromethane is prepared. The two solutions are combined to give, after rapid evaporation of the solvent, crystalline $Pd(CN)_2(t-C_4H_9NC)_2$ layers with a small amount of doping of $Pt(CN)_2(t-C_4H_9NC)_2$.
(see in this respect FIG. 15)

By increasing the degree of doping, the intensities of the emission bands at $\lambda_{max}$=419 nm and $\lambda_{max}$=515 nm can be changed relative to one another, enabling blue emission or broad-band white emission to be established.

The invention claimed is:

1. A light emitting device comprising
   (i) an anode,
   (ii) a cathode and
   (iii) an emitter layer, arranged between and in direct or indirect contact with the anode and cathode, comprising at least one complex of formula (I)

$$(NC)_nM(CNR)_m \quad (I)$$

wherein
   M is Pt(II), Pd(II), Rh(I), Ir(I), or Au(III);
   R is an alkyl, alkenyl, alkynyl, heteroaryl or —SO$_2$R' group, which optionally contains one or more functional groups wherein R' is a hydrocarbon group, which optionally contains heteroatoms; and
   n =m =2;
   wherein the proportion of complexes of formula (I) in the emitter layer is more than 10% by weight, based on the total weight of the emitter layer and
   wherein said device is insulated from the environment, so that ingress of gas from the environment into the emitter layer cannot occur;
   wherein two radicals CNR together form a radical CN—R"—NC, wherein R" is selected from alkylene, alkenylene, alkynylene, arylene, heteroarylene, wherein R" optionally contains one or more heteroatoms.

2. The light emitting device of claim 1, wherein it is an organic light-emitting device (OLED).

3. The light emitting device of claim 1, further comprising a hole-conductor layer and/or an electron-conductor layer.

4. The light emitting device of claim 1, further comprising a CsF or LiF interlayer.

5. The light emitting device of claim 1, wherein it is arranged on a substrate.

6. The light emitting device of claim 1, wherein M in formula (I) is Pt(II) or Pd(II).

7. The light emitting device of claim 1, wherein the proportion of complexes of formula (I) in the emitter layer is more than 30% by weight, based on the total weight of the emitter layer.

8. The light emitting device of claim 1, wherein the proportion of complexes of formula (I) in the emitter layer is more than 80% by weight, based on the total weight of the emitter layer.

9. The light emitting device of claim 1, wherein the complex of formula (I) in the emitter layer is bonded to a polymer.

10. The light emitting device of claim 9, wherein the bonding to the polymer takes place via polymerisable groups of the radicals R.

11. The light emitting device of claim 9, wherein an emitter layer is applied which comprises a polymer to which complexes of formula (I) are bonded, and the complexes are present in a concentration at which metal-metal interactions are able to form.

12. The light emitting device of claim 1, wherein it comprises, as emitter, the compound
dicyanobis(1,3-diisocyanopropane)platinum(II), $Pt(CN)_2(CNCH_2CH_2CH_2NC)$.

13. The light emitting device of claim 1, wherein it is a display and/or a light device.

14. A process for producing the light-emitting device of claim 1, wherein at least one complex of the formula (I) is introduced into the emitter layer by means of vacuum sublimation.

15. A process for producing the light-emitting device of claim 1, wherein at least one complex of the formula (I) is introduced into the emitter layer by wet-chemical methods.

16. A process for producing the light-emitting device of claim 1, wherein at least one complex of the formula (I) is applied as a colloidal suspension.

17. A light emitting device comprising
(i) an anode,
(ii) a cathode and
(iii) an emitter layer, arranged between and in direct or indirect contact with the anode and cathode, comprising at least two different complexes of formula (I)

$$(NC)_nM(CNR)_m \quad (I)$$

wherein
M is (Pt(II), Pd(II), Rh(I), Ir(I), or Au(III));
R is an alkyl, alkenyl, alkynyl, heteroaryl or —SO$_2$R' group, which optionally contains one or more functional groups wherein R' is a hydrocarbon group, which optionally contains heteroatoms; and
n =m =2;
wherein the proportion of complexes of formula (I) in the emitter layer is more than 10% by weight, based on the total weight of the emitter layer and
wherein said device is insulated from the environment, so that ingress of gas from the environment into the emitter layer cannot occur.

18. The light emitting device of claim 17, wherein the emitter layer comprises at least one complex of the formul (I) where M=Pt and at least one complex of the formula (I) where M=Pd.

19. The light emitting device of claim 17, wherein the at least two different complexes of the formula (I) are present in a columnar structure in the emitter layer.

20. A light emitting device comprising
(i) an anode,
(ii) a cathode and
(iii) an emitter layer, arranged between and in direct or indirect contact with the anode and cathode, comprising at least one complex of-formula (I)

$$(NC)_nM(CNR)_m \quad (I)$$

wherein
M is (Pt(II), Pd(II), Rh(I), Ir(I), or Au(III));
R is an alkenyl, alkynyl, heteroaryl or —SO$_2$R' group, which optionally contains one or more functional groups wherein R' is a hydrocarbon group, which optionally contains heteroatoms; and
n =m =2;
wherein the proportion of complexes of formula (I) in the emitter layer is more than 10% by weight, based on the total weight of the emitter layer and
wherein said device is insulated from the environment, so that ingress of gas from the environment into the emitter layer cannot occur.

* * * * *